(12) United States Patent
Kitabayashi et al.

(10) Patent No.: US 7,741,100 B2
(45) Date of Patent: Jun. 22, 2010

(54) METHOD FOR HIGHLY EXPRESSING RECOMBINANT GLUCOSE DEHYDROGENASE DERIVED FROM FILAMENTOUS FUNGI

(75) Inventors: Masao Kitabayashi, Tsuruga (JP); Yuji Tsuji, Tsuruga (JP); Hiroshi Kawaminami, Tsuruga (JP); Takahide Kishimoto, Tsuruga (JP); Yoshiaki Nishiya, Tsuruga (JP)

(73) Assignee: Toyo Boseki Kabushiki Kaisha, Osaka-shi (JP)

( * ) Notice: Subject to any disclaimer, the term of this patent is extended or adjusted under 35 U.S.C. 154(b) by 105 days.

(21) Appl. No.: 11/692,648

(22) Filed: Mar. 28, 2007

(65) Prior Publication Data

US 2008/0014611 A1 Jan. 17, 2008

Related U.S. Application Data

(60) Provisional application No. 60/788,252, filed on Mar. 31, 2006, provisional application No. 60/868,276, filed on Dec. 1, 2006.

(51) Int. Cl.
*C12N 1/20* (2006.01)
*C12N 15/00* (2006.01)
*C12N 9/04* (2006.01)
*C07H 21/02* (2006.01)

(52) U.S. Cl. ............... 435/252.3; 435/320.1; 435/190; 536/23.1

(58) Field of Classification Search ............... 536/23.2; 435/183, 252.3, 320.1, 52.3, 190
See application file for complete search history.

(56) References Cited

U.S. PATENT DOCUMENTS

| 4,877,733 | A | 10/1989 | Takahashi et al. | |
|---|---|---|---|---|
| 5,723,284 | A | 3/1998 | Ye | |
| 7,371,836 | B2 * | 5/2008 | Desnoyers et al. | ......... 536/23.1 |
| 2004/0023330 | A1 | 2/2004 | Sode | |
| 2006/0063217 | A1 | 3/2006 | Omura et al. | |
| 2007/0105174 | A1 * | 5/2007 | Aiba | .................. 435/14 |
| 2008/0003628 | A1 | 1/2008 | Kitabayashi et al. | |
| 2008/0014612 | A1 | 1/2008 | Tsuji et al. | |
| 2008/0020426 | A1 | 1/2008 | Aiba et al. | |
| 2008/0090278 | A1 | 4/2008 | Kitabayashi et al. | |

FOREIGN PATENT DOCUMENTS

| EP | 0 800 086 B1 | 1/2003 |
|---|---|---|
| EP | 1 584 675 A1 | 10/2005 |
| EP | 1 862 543 A1 | 12/2007 |
| JP | 05-304963 A | 11/1993 |
| JP | 10-010130 A | 1/1998 |
| JP | 2002-360259 A | 12/2002 |
| WO | WO 02/36779 A1 | 5/2002 |
| WO | WO 03/012071 A2 | 2/2003 |
| WO | WO 2004-058958 A1 | 7/2004 |
| WO | WO 2006-101239 A1 | 9/2006 |

OTHER PUBLICATIONS

Machida et al., Nature, 438: 1157-1161 (2005).
Bak et al., *Biochimica et Biophysica Acta*, 139: 265-276 (1967).
Bak, *Biochimica et Biophysica Acta*, 139: 277-293 (1967).
Bak, *Biochimica et Biophysica Acta*, 146: 317-327 (1967).
Bak et al., *Biochimica et Biophysica Acta*, 146: 328-335 (1967).
Belenky et al., *Antibiotiki*, 18: 602-603 (Jul. 1964).
Elzainy et al., *Ann. Microbiol. Enzimol.*, 43: 169-179 (1993).
Müller, *Arch. Microbiol.*, 144: 151-157 (1986).
Scognamiglio et al., *Journal of Fluorescence*, 14(5): 491-498 (Sep. 2004).
Database UNIPROT, Entry Name "Q2USF2_ASPOR," Accession No. Q2USF2 (Jan. 24, 2006).
Schrank et al., *Gene*, 73: 121-130 (1988).
Sirakova et al., *Infection and Immunity*, 62(10): 4208-4218 (Oct. 1994).
Wicher et al., *Appl. Microbiol. Biotechnol.*, 55: 578-584 (2001).
Whitwam et al., *Biochemical and Biophysical Research Communications*, 216(3): 1013-1017 (Nov. 22, 1995).

* cited by examiner

*Primary Examiner*—Maryam Monshipouri
(74) *Attorney, Agent, or Firm*—Leydig, Voit & Mayer, Ltd.

(57) ABSTRACT

The present invention provides a method for highly expressing a recombinant FAD-GDH protein derived from filamentous fungi, protein obtained by the method, and a regent for measuring glucose using the protein. According to the invention, the FAD-GDH can be highly expressed by altering DNA sequence coding for a signal peptide of FAD-GDH gene isolated from *Aspergillus oryzae*. FAD-GDH can be stably produced by adjusting pH of 7.1 to 7.3 during culture production.

6 Claims, 7 Drawing Sheets

Fig. 1

SignalP-NN result:

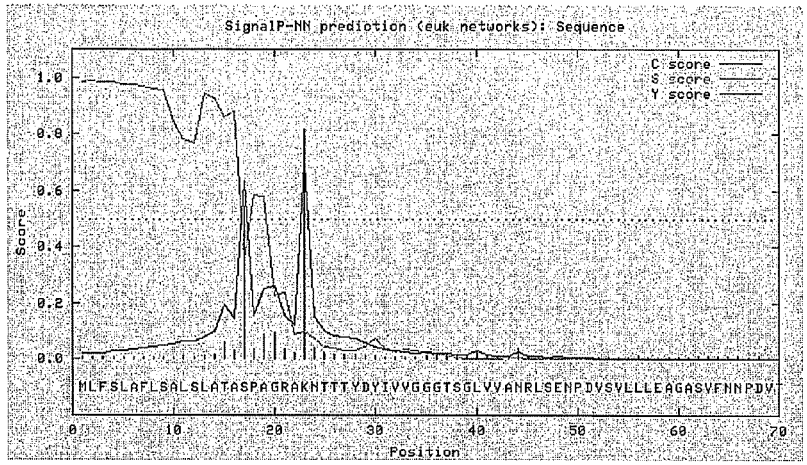

```
>Sequence              length = 70
# Measure   Position   Value    Cutoff    signal peptide?
  max. C      23       0.814    0.32      YES    (cleavage site)
  max. Y      23       0.700    0.33      YES    (score of cleavage sate
in view of S score)
  max. S       2       0.990    0.87      YES    (signal peptide region)
  mean S     1-22      0.767    0.48      YES
       D     1-22      0.733    0.43      YES
# Most likely cleavage site between pos. 22 and 23: GRA-KN
```

SignalP-HMM result:

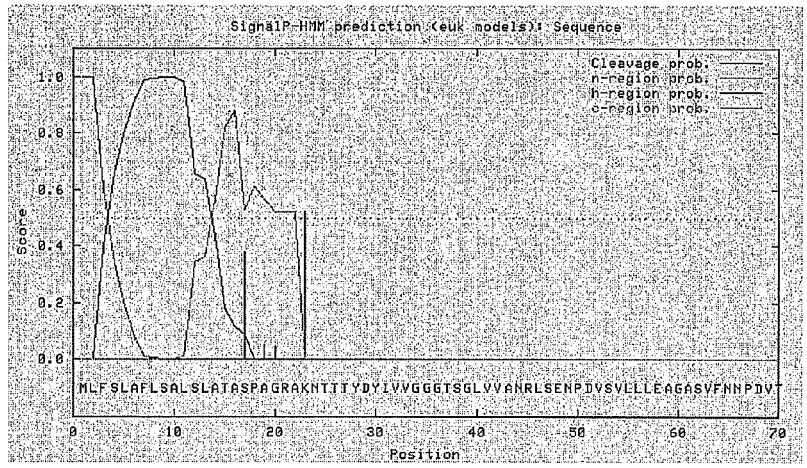

h-region prob. : hydrophobic region, c-region prob. : hydrophobic region through cleavage site
>Sequence
Prediction: Signal peptide
Signal peptide probability: 1.000
Signal anchor probability: 0.000
Max cleavage site probability: 0.520 between pos. 22 and 23

SEQUENCE LISTING

<160> NUMBER OF SEQ ID NOS: 18

<210> SEQ ID NO 1
<211> LENGTH: 1767
<212> TYPE: DNA
<213> ORGANISM: Aspergillus oryzae

<400> SEQUENCE: 1

```
atgctcttct cactggcatt cctgagtgcc ctgtcgctgg ccacggcatc accggctgga      60
cgggccaaga acactacgac atacgactac atcgttgtgg gaggcggcac aagtggtctt     120
gtggtcgcaa atcgcctttc tgagaacccc gatgtctccg ttcttctgct tgaggccggt     180
gcttctgtgt tcaacaaccc ggacgtaacc aacgctaacg gttatggatt ggcctttggc     240
tcggccatcg actggcagta ccagtctatt aaccaaagct atgcaggagg taaacagcaa     300
```

-continued

```
gttctgcgtg ctggtaaggc ccttggagga accagtacaa tcaatggaat ggcctatacc    360
cgcgcagagg atgtccagat tgacgtttgg cagaaacttg aaacgaagg ttggacgtgg     420
aaagatctcc taccatacta cctgaagagt gaaaacttga cggccccta cagctctcag    480
gttgctgctg gcgctgctta taaccctgcc gtgaatggaa agaaggtcc tctcaaggtc    540
ggctggtcgg aagcctggc ctccggtaat ctgtcagttg ctctgaaccg tacgttccaa    600
gccatggagg atgtcaatgg aggcaagatg cgtggcttca acatctaccc atccaccctc    660
gacgttgacc tcaatgtccg cgaagatgca gcccgggcat actacttccc ttatgatgac    720
aggaagaacc ttcacctgct ggagaacacc actgccaacc gccttttctg gaagaacggc    780
tctgctgagg aagctattgc ggatggtgtc gagatcacct ccgctgatgg caaggtcact    840
cgtgtgcatg caaagaaaga ggtcatcatc tctgctggtg ccctgcggtc tcctctcatt    900
ctcgagcttt caggagttgg aaacccaacc atcctcaaaa agaacaacat aaccccacgt    960
gtcgatctcc ccaccgttgg ggagaacctc caagaccagt tcaacaacgg catggctggc   1020
gaaggatacg gcgtccttgc cggtgcctca accgtgacct acccttccat ctccgacgtc   1080
ttcggtaacg agactgactc tatcgttgca tctctccgat ctcaactctc cgactacgcc   1140
gccgcgaccg tcaaggtcag caacggccac atgaagcagg aggaccttga gcgcctctac   1200
cagctccaat ttgacctcat cgtcaaggac aaggtcccta tcgccgagat cctcttccac   1260
cccggtggtg gaaacgccgt gtcctccgaa ttctggggct tgcttccctt cgcccgtggc   1320
aacatccaca ttagctccaa tgacccgact gctcccgccg ccatcaaccc taactacttt   1380
atgttcgaat gggacggcaa gagccaggcc ggtatcgcca gtacatcag gaagattctc    1440
cgcagcgcac cattgaacaa acttattgcg aaggaaacca gcccggtct ctctgagatt    1500
ccggccactg ctgcggatga aagtgggtt gaatggctca aggctaacta tcgttccaac   1560
ttccaccccg tcggaactgc tgccatgatg cctcgttcca ttggtggcgt tgttgataac   1620
cgtctccggg tctatggtac cagcaatgtt cgcgtcgtag atgcgtctgt cctgccctcc   1680
caggttttgcg gccacttggt tagcacgctt tatgccgttg ccgagcgcgc ttccgacttg   1740
attaaggagg atgcgaagag tgcttag                                        1767
```

<210> SEQ ID NO 2
<211> LENGTH: 588
<212> TYPE: PRT
<213> ORGANISM: Aspergillus oryzae
<400> SEQUENCE: 2

```
Met Leu Phe Ser Leu Ala Phe Leu Ser Ala Leu Ser Leu Ala Thr Ala
1               5                   10                  15

Ser Pro Ala Gly Arg Ala Lys Asn Thr Thr Thr Tyr Asp Tyr Ile Val
            20                  25                  30

Val Gly Gly Gly Thr Ser Gly Leu Val Val Ala Asn Arg Leu Ser Glu
        35                  40                  45

Asn Pro Asp Val Ser Val Leu Leu Glu Ala Gly Ala Ser Val Phe
    50                  55                  60

Asn Asn Pro Asp Val Thr Asn Ala Asn Gly Tyr Gly Leu Ala Phe Gly
65                  70                  75                  80

Ser Ala Ile Asp Trp Gln Tyr Gln Ser Ile Asn Gln Ser Tyr Ala Gly
                85                  90                  95

Gly Lys Gln Gln Val Leu Arg Ala Gly Lys Ala Leu Gly Gly Thr Ser
            100                 105                 110
```

-continued

```
Thr Ile Asn Gly Met Ala Tyr Thr Arg Ala Glu Asp Val Gln Ile Asp
        115                 120                 125

Val Trp Gln Lys Leu Gly Asn Glu Gly Trp Thr Trp Lys Asp Leu Leu
    130                 135                 140

Pro Tyr Tyr Leu Lys Ser Glu Asn Leu Thr Ala Pro Thr Ser Ser Gln
145                 150                 155                 160

Val Ala Ala Gly Ala Ala Tyr Asn Pro Ala Val Asn Gly Lys Glu Gly
                165                 170                 175

Pro Leu Lys Val Gly Trp Ser Gly Ser Leu Ala Ser Gly Asn Leu Ser
            180                 185                 190

Val Ala Leu Asn Arg Thr Phe Gln Ala Met Glu Asp Val Asn Gly Gly
        195                 200                 205

Lys Met Arg Gly Phe Asn Ile Tyr Pro Ser Thr Leu Asp Val Asp Leu
    210                 215                 220

Asn Val Arg Glu Asp Ala Ala Arg Ala Tyr Tyr Phe Pro Tyr Asp Asp
225                 230                 235                 240

Arg Lys Asn Leu His Leu Leu Glu Asn Thr Thr Ala Asn Arg Leu Phe
                245                 250                 255

Trp Lys Asn Gly Ser Ala Glu Glu Ala Ile Ala Asp Gly Val Glu Ile
            260                 265                 270

Thr Ser Ala Asp Gly Lys Val Thr Arg Val His Ala Lys Lys Glu Val
        275                 280                 285

Ile Ile Ser Ala Gly Ala Leu Arg Ser Pro Leu Ile Leu Glu Leu Ser
    290                 295                 300

Gly Val Gly Asn Pro Thr Ile Leu Lys Lys Asn Asn Ile Thr Pro Arg
305                 310                 315                 320

Val Asp Leu Pro Thr Val Gly Glu Asn Leu Gln Asp Gln Phe Asn Asn
                325                 330                 335

Gly Met Ala Gly Glu Gly Tyr Gly Val Leu Ala Gly Ala Ser Thr Val
            340                 345                 350

Thr Tyr Pro Ser Ile Ser Asp Val Phe Gly Asn Glu Thr Asp Ser Ile
        355                 360                 365

Val Ala Ser Leu Arg Ser Gln Leu Ser Asp Tyr Ala Ala Ala Thr Val
    370                 375                 380

Lys Val Ser Asn Gly His Met Lys Gln Glu Asp Leu Glu Arg Leu Tyr
385                 390                 395                 400

Gln Leu Gln Phe Asp Leu Ile Val Lys Asp Lys Val Pro Ile Ala Glu
                405                 410                 415

Ile Leu Phe His Pro Gly Gly Asn Ala Val Ser Ser Glu Phe Trp
            420                 425                 430

Gly Leu Leu Pro Phe Ala Arg Gly Asn Ile His Ile Ser Ser Asn Asp
        435                 440                 445

Pro Thr Ala Pro Ala Ala Ile Asn Pro Asn Tyr Phe Met Phe Glu Trp
450                 455                 460

Asp Gly Lys Ser Gln Ala Gly Ile Ala Lys Tyr Ile Arg Lys Ile Leu
465                 470                 475                 480

Arg Ser Ala Pro Leu Asn Lys Leu Ile Ala Lys Glu Thr Lys Pro Gly
                485                 490                 495

Leu Ser Glu Ile Pro Ala Thr Ala Ala Asp Glu Lys Trp Val Glu Trp
            500                 505                 510

Leu Lys Ala Asn Tyr Arg Ser Asn Phe His Pro Val Gly Thr Ala Ala
        515                 520                 525

Met Met Pro Arg Ser Ile Gly Gly Val Val Asp Asn Arg Leu Arg Val
```

| | | | |
|---|---|---|---|
| | 530 | 535 | 540 |

Tyr Gly Thr Ser Asn Val Arg Val Val Asp Ala Ser Val Leu Pro Phe
545 550 555 560

Gln Val Cys Gly His Leu Val Ser Thr Leu Tyr Ala Val Ala Glu Arg
565 570 575

Ala Ser Asp Leu Ile Lys Glu Asp Ala Lys Ser Ala
580 585

<210> SEQ ID NO 3
<211> LENGTH: 1779
<212> TYPE: DNA
<213> ORGANISM: Aspergillus oryzae

<400> SEQUENCE: 3

| | |
|---|---|
| atgctcttct cactggcatt cctgagtgcc ctgtcgctgg ccacggcatc accggctgga | 60 |
| cgggccaaga acactacgac atacgactac atcgttgtgg gaggcggcac aagtggtctt | 120 |
| gtggtcgcaa atcgcctttc tgagaacccc gatgtctccg ttcttctgct tgaggccggt | 180 |
| gcttctgtgt tcaacaaccc ggacgtaacc aacgctaacg ttatggatt ggccttttggc | 240 |
| tcggccatcg actggcagta ccagtctatt aaccaaagct atgcaggagg taaacagcaa | 300 |
| gttctgcgtg ctggtaaggc ccttggagga accagtacaa tcaatggaat ggcctatacc | 360 |
| cgcgcagagg atgtccagat tgacgtttgg cagaaacttg gaaacgaagg ttggacgtgg | 420 |
| aaagatctcc taccatacta cctgaagagt gaaaacttga cggcccctac cagctctcag | 480 |
| gttgctgctg gcgctgctta taccctgccg gtgaatggaa agaaggtcc tctcaaggtc | 540 |
| ggctggtcgg aagcctggc ctccggtaat ctgtcagttg ctctgaaccg tacgttccaa | 600 |
| gccgctggtg ttccatgggt tgaggatgtc aatggaggca gatgcgtgg cttcaacatc | 660 |
| tacccatcca ccctcgacgt tgacctcaat gtccgcgaag atgcagcccg gcatactac | 720 |
| ttcccttatg atgacaggaa gaaccttcac ctgctggaga acaccactgc caaccgcctt | 780 |
| ttctggaaga acggctctgc tgaggaagct attgcggatg tgtcgagat caccctccgct | 840 |
| gatggcaagg tcactcgtgt gcatgcaaag aagaggtca tcatctctgc tggtgccctg | 900 |
| cggtctcctc tcattctcga gctttcagga gttggaaacc caaccatcct caaaaagaac | 960 |
| aacataaccc cacgtgtcga tctcccccacc gttggggaga acctccaaga ccagttcaac | 1020 |
| aacggcatgg ctggcgaagg atacggcgtc cttgccggtg cctcaaccgt gacctaccct | 1080 |
| tccatctccg acgtcttcgg taacgagact gactctatcg ttgcatctct ccgatctcaa | 1140 |
| ctctccgact acgccgccgc gaccgtcaag gtcagcaacg ccacatgaa gcaggaggac | 1200 |
| cttgagcgcc tctaccagct ccaatttgac ctcatcgtca aggacaaggt ccctatcgcc | 1260 |
| gagatcctct tccaccccgg tggtggaaac gccgtgtcct ccgaattctg gggcttgctt | 1320 |
| cccttcgccc gtggcaacat ccacattagc tccaatgacc cgactgctcc cgccgccatc | 1380 |
| aaccctaact actttatgtt cgaatgggac ggcaagagcc aggccggtat cgccaagtac | 1440 |
| atcaggaaga ttctccgcag cgcaccattg aacaaactta ttgcgaagga aaccaagccc | 1500 |
| ggtctctctg agattccggc cactgctgcg gatgagaagt gggttgaatg gctcaaggct | 1560 |
| aactatcgtt ccaacttcca ccccgtcgga actgctgcca tgatgcctcg ttccattggt | 1620 |
| ggcgttgttg ataaccgtct ccgggtctat ggtaccagca atgttcgcgt cgtagatgcg | 1680 |
| tctgtcctgc ccttccaggt ttgcggccac ttggttagca cgctttatgc cgttgccgag | 1740 |
| cgcgcttccg acttgattaa ggaggatgcg aagagtgct | 1779 |

<210> SEQ ID NO 4
<211> LENGTH: 593
<212> TYPE: PRT
<213> ORGANISM: Aspergillus oryzae

<400> SEQUENCE: 4

| Met | Leu | Phe | Ser | Leu | Ala | Phe | Leu | Ser | Ala | Leu | Ser | Leu | Ala | Thr | Ala |
|---|---|---|---|---|---|---|---|---|---|---|---|---|---|---|---|
| 1 | | | | 5 | | | | | 10 | | | | | 15 | |

Ser Pro Ala Gly Arg Ala Lys Asn Thr Thr Tyr Asp Tyr Ile Val
            20                  25                  30

Val Gly Gly Gly Thr Ser Gly Leu Val Val Ala Asn Arg Leu Ser Glu
        35                  40                  45

Asn Pro Asp Val Ser Val Leu Leu Glu Ala Gly Ala Ser Val Phe
50                  55                  60

Asn Asn Pro Asp Val Thr Asn Ala Asn Gly Tyr Gly Leu Ala Phe Gly
65                  70                  75                  80

Ser Ala Ile Asp Trp Gln Tyr Gln Ser Ile Asn Gln Ser Tyr Ala Gly
                85                  90                  95

Gly Lys Gln Gln Val Leu Arg Ala Gly Lys Ala Leu Gly Gly Thr Ser
            100                 105                 110

Thr Ile Asn Gly Met Ala Tyr Thr Arg Ala Glu Asp Val Gln Ile Asp
        115                 120                 125

Val Trp Gln Lys Leu Gly Asn Glu Gly Trp Thr Trp Lys Asp Leu Leu
130                 135                 140

Pro Tyr Tyr Leu Lys Ser Glu Asn Leu Thr Ala Pro Thr Ser Ser Gln
145                 150                 155                 160

Val Ala Ala Gly Ala Ala Tyr Asn Pro Ala Val Asn Gly Lys Glu Gly
                165                 170                 175

Pro Leu Lys Val Gly Trp Ser Gly Ser Leu Ala Ser Gly Asn Leu Ser
            180                 185                 190

Val Ala Leu Asn Arg Thr Phe Gln Ala Ala Gly Val Pro Trp Val Glu
        195                 200                 205

Asp Val Asn Gly Gly Lys Met Arg Gly Phe Asn Ile Tyr Pro Ser Thr
210                 215                 220

Leu Asp Val Asp Leu Asn Val Arg Glu Asp Ala Ala Arg Ala Tyr Tyr
225                 230                 235                 240

Phe Pro Tyr Asp Asp Arg Lys Asn Leu His Leu Leu Glu Asn Thr Thr
                245                 250                 255

Ala Asn Arg Leu Phe Trp Lys Asn Gly Ser Ala Glu Glu Ala Ile Ala
            260                 265                 270

Asp Gly Val Glu Ile Thr Ser Ala Asp Gly Lys Val Thr Arg Val His
        275                 280                 285

Ala Lys Lys Glu Val Ile Ile Ser Ala Gly Ala Leu Arg Ser Pro Leu
290                 295                 300

Ile Leu Glu Leu Ser Gly Val Gly Asn Pro Thr Ile Leu Lys Lys Asn
305                 310                 315                 320

Asn Ile Thr Pro Arg Val Asp Leu Pro Thr Val Gly Glu Asn Leu Gln
                325                 330                 335

Asp Gln Phe Asn Asn Gly Met Ala Gly Glu Gly Tyr Gly Val Leu Ala
            340                 345                 350

Gly Ala Ser Thr Val Thr Tyr Pro Ser Ile Ser Asp Val Phe Gly Asn
        355                 360                 365

Glu Thr Asp Ser Ile Val Ala Ser Leu Arg Ser Gln Leu Ser Asp Tyr
370                 375                 380

```
Ala Ala Ala Thr Val Lys Val Ser Asn Gly His Met Lys Gln Glu Asp
385                 390                 395                 400

Leu Glu Arg Leu Tyr Gln Leu Gln Phe Asp Leu Ile Val Lys Asp Lys
            405                 410                 415

Val Pro Ile Ala Glu Ile Leu Phe His Pro Gly Gly Asn Ala Val
        420                 425                 430

Ser Ser Glu Phe Trp Gly Leu Leu Pro Phe Ala Arg Gly Asn Ile His
        435                 440                 445

Ile Ser Ser Asn Asp Pro Thr Ala Pro Ala Ala Ile Asn Pro Asn Tyr
    450                 455                 460

Phe Met Phe Glu Trp Asp Gly Lys Ser Gln Ala Gly Ile Ala Lys Tyr
465                 470                 475                 480

Ile Arg Lys Ile Leu Arg Ser Ala Pro Leu Asn Lys Leu Ile Ala Lys
            485                 490                 495

Glu Thr Lys Pro Gly Leu Ser Glu Ile Pro Ala Thr Ala Ala Asp Glu
            500                 505                 510

Lys Trp Val Glu Trp Leu Lys Ala Asn Tyr Arg Ser Asn Phe His Pro
        515                 520                 525

Val Gly Thr Ala Ala Met Met Pro Arg Ser Ile Gly Gly Val Val Asp
530                 535                 540

Asn Arg Leu Arg Val Tyr Gly Thr Ser Asn Val Arg Val Val Asp Ala
545                 550                 555                 560

Ser Val Leu Pro Phe Gln Val Cys Gly His Leu Val Ser Thr Leu Tyr
                565                 570                 575

Ala Val Ala Glu Arg Ala Ser Asp Leu Ile Lys Glu Asp Ala Lys Ser
            580                 585                 590

Ala

<210> SEQ ID NO 5
<211> LENGTH: 34
<212> TYPE: DNA
<213> ORGANISM: Artificial Sequence
<220> FEATURE:
<223> OTHER INFORMATION: The sequence of designed polynucleotide
      described in Example 1

<400> SEQUENCE: 5
ggaattccat atgctcttct cactggcatt cctg                               34

<210> SEQ ID NO 6
<211> LENGTH: 35
<212> TYPE: DNA
<213> ORGANISM: Artificial Sequence
<220> FEATURE:
<223> OTHER INFORMATION: The sequence of designed polynucleotide
      described in Example 1

<400> SEQUENCE: 6
cgggatccga attggtacgg gacactgtcc ctacg                              35

<210> SEQ ID NO 7
<211> LENGTH: 37
<212> TYPE: DNA
<213> ORGANISM: Artificial Sequence
<220> FEATURE:
<223> OTHER INFORMATION: The sequence of designed polinucleotide
      described in Example 1

<400> SEQUENCE: 7
```

```
ggaattccat atgaagaaca ctacgacata cgactac                              37
```

<210> SEQ ID NO 8
<211> LENGTH: 37
<212> TYPE: DNA
<213> ORGANISM: Artificial Sequence
<220> FEATURE:
<223> OTHER INFORMATION: The sequence of designed polinucleotide
    described in Example 1

<400> SEQUENCE: 8

```
cacacaggaa acacatatga acactacgac atacgac                              37
```

<210> SEQ ID NO 9
<211> LENGTH: 1719
<212> TYPE: DNA
<213> ORGANISM: Aspergillus oryzae mutant

<400> SEQUENCE: 9

```
atgaagaaca ctacgacata cgactacatc gttgtgggag gcggcacaag tggtcttgtg      60
gtcgcaaatc gccttttctga gaaccccgat gtctccgttc ttctgcttga ggccggtgct    120
tctgtgttca caacccgga cgtaaccaac gctaacggtt atggattggc ctttggctcg     180
gccatcgact ggcagtacca gtctattaac caaagctatg caggaggtaa acagcaagtt    240
ctgcgtgctg gtaaggccct tggaggaacc agtacaatca atggaatggc ctatacccgc    300
gcagaggatg tccagattga cgtttggcag aaacttggaa cgaaggttg gacgtggaaa     360
gatctcctac atactacct gaagagtgaa aacttgacgg ccctaccag ctctcaggtt      420
gctgctggcg ctgcttataa ccctgccgtg aatggaaaag aaggtcctct caaggtcggc    480
tggtcgagga gcctggcctc cggtaatctg tcagttgctc tgaaccgtac gttccaagcc    540
gctggtgttc catgggttga ggatgtcaat ggaggcaaga tgcgtggctt caacatctac    600
ccatccaccc tcgacgttga cctcaatgtc cgcgaagatg cagcccgggc atactacttc    660
ccttatgatg acaggaagaa ccttcacctg ctggagaaca ccactgccaa ccgccttttc    720
tggaagaacg gctctgctga ggaagctatt gcggatggtg tcgagatcac ctccgctgat    780
ggcaaggtca ctcgtgtgca tgcaaagaaa gaggtcatca tctctgctgg tgccctgcgg    840
tctcctctca ttctcgagct ttcaggagtt ggaaacccaa ccatcctcaa aaagaacaac    900
ataaccccac gtgtcgatct ccccaccgtt ggggagaacc tccaagacca gttcaacaac    960
ggcatggctg gcgaaggata cggcgtcctt gccggtgcct caaccgtgac ctacccttcc   1020
atctccgacg tcttcggtaa cgagactgac tctatcgttg catctctccg atctcaactc   1080
tccgactacg ccgccgcgac cgtcaaggtc agcaacggcc acatgaagca ggaggacctt   1140
gagcgcctct accagctcca atttgacctc atcgtcaagg acaaggtccc tatcgccgag   1200
atcctcttcc accccggtgg tggaaacgcc gtgtcctccg aattctgggg cttgcttccc   1260
ttcgcccgtg gcaacatcca cattagctcc aatgacccga ctgctcccgc cgccatcaac   1320
cctaactact ttatgttcga atgggacggc aagagccagg ccggtatcgc caagtacatc   1380
aggaagattc tccgcagcgc accattgaac aaacttattg cgaaggaaac caagcccggt   1440
ctctctgaga ttccggccac tgctgcggat gagaagtggg ttgaatggct caaggctaac   1500
tatcgttcca acttccaccc cgtcggaact gctgccatga tgcctcgttc cattggtggc   1560
gttgttgata accgtctccg ggtctatggt accagcaatg ttcgcgtcgt agatgcgtct   1620
gtcctgccct tccaggtttg cggccacttg tgcagcacgc tttatgccgt tgccgagcgc   1680
```
gcttccgact tgattaagga ggatgcgaag agtgcttag                                   1719

<210> SEQ ID NO 10
<211> LENGTH: 572
<212> TYPE: PRT
<213> ORGANISM: Aspergillus oryzae mutant

<400> SEQUENCE: 10

| | | | | | | | | | | | | | | |
|---|---|---|---|---|---|---|---|---|---|---|---|---|---|---|
| Met | Lys | Asn | Thr | Thr | Tyr | Asp | Tyr | Ile | Val | Val | Gly | Gly | Gly | Thr |
| 1 | | | | 5 | | | | | 10 | | | | | 15 |
| Ser | Gly | Leu | Val | Val | Ala | Asn | Arg | Leu | Ser | Glu | Asn | Pro | Asp | Val | Ser |
| | | | 20 | | | | | 25 | | | | | 30 | | |
| Val | Leu | Leu | Leu | Glu | Ala | Gly | Ala | Ser | Val | Phe | Asn | Asn | Pro | Asp | Val |
| | | | 35 | | | | 40 | | | | | 45 | | | |
| Thr | Asn | Ala | Asn | Gly | Tyr | Gly | Leu | Ala | Phe | Gly | Ser | Ala | Ile | Asp | Trp |
| 50 | | | | | 55 | | | | | 60 | | | | | |
| Gln | Tyr | Gln | Ser | Ile | Asn | Gln | Ser | Tyr | Ala | Gly | Gly | Lys | Gln | Gln | Val |
| 65 | | | | 70 | | | | | 75 | | | | | 80 | |
| Leu | Arg | Ala | Gly | Lys | Ala | Leu | Gly | Gly | Thr | Ser | Thr | Ile | Asn | Gly | Met |
| | | | | 85 | | | | | 90 | | | | | 95 | |
| Ala | Tyr | Thr | Arg | Ala | Glu | Asp | Val | Gln | Ile | Asp | Val | Trp | Gln | Lys | Leu |
| | | | 100 | | | | | 105 | | | | | 110 | | |
| Gly | Asn | Glu | Gly | Trp | Thr | Trp | Lys | Asp | Leu | Leu | Pro | Tyr | Tyr | Leu | Lys |
| | | | 115 | | | | | 120 | | | | | 125 | | |
| Ser | Glu | Asn | Leu | Thr | Ala | Pro | Thr | Ser | Ser | Gln | Val | Ala | Ala | Gly | Ala |
| | 130 | | | | | 135 | | | | | 140 | | | | |
| Ala | Tyr | Asn | Pro | Ala | Val | Asn | Gly | Lys | Glu | Gly | Pro | Leu | Lys | Val | Gly |
| 145 | | | | | 150 | | | | | 155 | | | | | 160 |
| Trp | Ser | Arg | Ser | Leu | Ala | Ser | Gly | Asn | Leu | Ser | Val | Ala | Leu | Asn | Arg |
| | | | | 165 | | | | | 170 | | | | | 175 | |
| Thr | Phe | Gln | Ala | Ala | Gly | Val | Pro | Trp | Val | Glu | Asp | Val | Asn | Gly | Gly |
| | | | 180 | | | | | 185 | | | | | 190 | | |
| Lys | Met | Arg | Gly | Phe | Asn | Ile | Tyr | Pro | Ser | Thr | Leu | Asp | Val | Asp | Leu |
| | | 195 | | | | | 200 | | | | | 205 | | | |
| Asn | Val | Arg | Glu | Asp | Ala | Ala | Arg | Ala | Tyr | Tyr | Phe | Pro | Tyr | Asp | Asp |
| 210 | | | | | 215 | | | | | 220 | | | | | |
| Arg | Lys | Asn | Leu | His | Leu | Leu | Glu | Asn | Thr | Thr | Ala | Asn | Arg | Leu | Phe |
| 225 | | | | | 230 | | | | | 235 | | | | | 240 |
| Trp | Lys | Asn | Gly | Ser | Ala | Glu | Glu | Ala | Ile | Ala | Asp | Gly | Val | Glu | Ile |
| | | | | 245 | | | | | 250 | | | | | 255 | |
| Thr | Ser | Ala | Asp | Gly | Lys | Val | Thr | Arg | Val | His | Ala | Lys | Lys | Glu | Val |
| | | | 260 | | | | | 265 | | | | | 270 | | |
| Ile | Ile | Ser | Ala | Gly | Ala | Leu | Arg | Ser | Pro | Leu | Ile | Leu | Glu | Leu | Ser |
| 275 | | | | | 280 | | | | | 285 | | | | | |
| Gly | Val | Gly | Asn | Pro | Thr | Ile | Leu | Lys | Lys | Asn | Asn | Ile | Thr | Pro | Arg |
| | 290 | | | | | 295 | | | | | 300 | | | | |
| Val | Asp | Leu | Pro | Thr | Val | Gly | Glu | Asn | Leu | Gln | Asp | Gln | Phe | Asn | Asn |
| 305 | | | | | 310 | | | | | 315 | | | | | 320 |
| Gly | Met | Ala | Gly | Glu | Gly | Tyr | Gly | Val | Leu | Ala | Gly | Ala | Ser | Thr | Val |
| | | | | 325 | | | | | 330 | | | | | 335 | |
| Thr | Tyr | Pro | Ser | Ile | Ser | Asp | Val | Phe | Gly | Asn | Glu | Thr | Asp | Ser | Ile |
| | | | 340 | | | | | 345 | | | | | 350 | | |
| Val | Ala | Ser | Leu | Arg | Ser | Gln | Leu | Ser | Asp | Tyr | Ala | Ala | Ala | Thr | Val |
| | | 355 | | | | | 360 | | | | | 365 | | | |

```
Lys Val Ser Asn Gly His Met Lys Gln Glu Asp Leu Glu Arg Leu Tyr
            370                 375                 380
Gln Leu Gln Phe Asp Leu Ile Val Lys Asp Lys Val Pro Ile Ala Glu
385                 390                 395                 400
Ile Leu Phe His Pro Gly Gly Asn Ala Val Ser Ser Glu Phe Trp
                405                 410                 415
Gly Leu Leu Pro Phe Ala Arg Gly Asn Ile His Ile Ser Ser Asn Asp
                420                 425                 430
Pro Thr Ala Pro Ala Ala Ile Asn Pro Asn Tyr Phe Met Phe Glu Trp
                435                 440                 445
Asp Gly Lys Ser Gln Ala Gly Ile Ala Lys Tyr Ile Arg Lys Ile Leu
            450                 455                 460
Arg Ser Ala Pro Leu Asn Lys Leu Ile Ala Lys Glu Thr Lys Pro Gly
465                 470                 475                 480
Leu Ser Glu Ile Pro Ala Thr Ala Ala Asp Glu Lys Trp Val Glu Trp
                485                 490                 495
Leu Lys Ala Asn Tyr Arg Ser Asn Phe His Pro Val Gly Thr Ala Ala
                500                 505                 510
Met Met Pro Arg Ser Ile Gly Gly Val Val Asp Asn Arg Leu Arg Val
                515                 520                 525
Tyr Gly Thr Ser Asn Val Arg Val Val Asp Ala Ser Val Leu Pro Phe
            530                 535                 540
Gln Val Cys Gly His Leu Cys Ser Thr Leu Tyr Ala Val Ala Glu Arg
545                 550                 555                 560
Ala Ser Asp Leu Ile Lys Glu Asp Ala Lys Ser Ala
                565                 570

<210> SEQ ID NO 11
<211> LENGTH: 1704
<212> TYPE: DNA
<213> ORGANISM: Aspergillus terreus

<400> SEQUENCE: 11
atgaaatatg attatatcgt tattggaggc ggtaccagcg gtttggccgt cgcaaaccgt      60
ctatcggagg acccaagcgt gaacgtactc attctggagg ccggtggctc ggtctggaac     120
aatcccaatg tcacaaacgt gaatggctat gggcttgcat tgggtctgaa cattgactgg     180
caataccagt ccgtcaacca gccatatgga ggcaacgtca gtcaagtgct gcgtgccggc     240
aaggcccttg gtggtactag tactattaac ggtatggcct ataccgcgc cgaggatgtc      300
cagatcgacg cctgggaaac cattggcaac acaggatgga cgtggaagaa tctgttccct     360
tactatcgga gagcgagaa cttcactgtc cctaccaaat cgcagacttc tcttggagcg      420
tcgtatgaag ctggagccca cggccacgag ggtccccttg acgttgcctt cactcagatc     480
gagtcgaaca acctgaccac ctacctcaac cgtaccttcc agggcatggg actcccatgg     540
actgaggacg tcaatggcgg aaagatgcgc ggctttaacc tataccctc caccgtgaat     600
cttgaggagt atgttcgcga agacgccgct cgtgcatact actggcctta caagtcccgt     660
cccaacctgc atgtcctgct caacactttt gccaaccgga ttgtgtggga cggcgaagcc     720
cgtgatggcg acatcactgc cagtggtgtc gagatcactt ccaggaacgg cactgttcgt     780
gttatcaatg cggagaagga agtcattgtc tctgccggcg ccttgaagtc cccggctatc     840
cttgaacttt ccggaattgg caaccctagc gttcttgaca gtacaacat ccccgtcaag      900
gtcaacctcc ctactgtagg tgagaacctt caggaccagg tgaacagcca catggatgcg     960
```

-continued

```
tcgggcaaca cttccatctc tggaaccaag gcagtctctt accccgatgt ctatgacgtc    1020
ttcggtgacg aagccgagtc ggtcgccaaa cagatccgtg ccagcctgaa gcaatacgcc    1080
gccgacaccg cccaggccaa cggaaacatc atgaaggccg ccgatctgga gcgtctcttc    1140
gaggtccagt atgaccttat tttcaagggc agagtcccaa ttgcagaagt cctcaactat    1200
cctggcagcg cgacgtccgt gtttgcagaa ttctgggccc tccttccctt cgctcgggga    1260
agtgttcaca tcggttcttc aaacccggtc gagtttcctg tcatcaaccc caactatttc    1320
atgctcgact gggacgcgaa gagctacgtc gccgttgcaa agtatatccg ccgctcgttc    1380
gagagctacc ctctcagcag catcgttaag gagtctaccc ctggctatga tgttatcccc    1440
cggaacgctt ctgaacagag ctggaaagaa tgggtctttg ataagaacta tcgttctaac    1500
ttccatcccg tcggcacggc tgccatgatg cctcgtgaaa ttggcggtgt cgtggacgag    1560
cgtctgaatg tctatggtac tacgaacgtc agagttgtcg atgcctcggt gcttccgttc    1620
caggtctgcg gtcatttggt gagcacccta tacgctgtgg ccgaacgggc agcggatctc    1680
atcaaggccg atgctggtcg tcgt                                           1704
```

<210> SEQ ID NO 12
<211> LENGTH: 568
<212> TYPE: PRT
<213> ORGANISM: Aspergillus terreus

<400> SEQUENCE: 12

```
Met Lys Tyr Asp Tyr Ile Val Ile Gly Gly Thr Ser Gly Leu Ala
1               5                   10                  15

Val Ala Asn Arg Leu Ser Glu Asp Pro Ser Val Asn Val Leu Ile Leu
            20                  25                  30

Glu Ala Gly Gly Ser Val Trp Asn Asn Pro Asn Val Thr Asn Val Asn
        35                  40                  45

Gly Tyr Gly Leu Ala Phe Gly Ser Asp Ile Asp Trp Gln Tyr Gln Ser
    50                  55                  60

Val Asn Gln Pro Tyr Gly Gly Asn Val Ser Gln Val Leu Arg Ala Gly
65                  70                  75                  80

Lys Ala Leu Gly Gly Thr Ser Thr Ile Asn Gly Met Ala Tyr Thr Arg
                85                  90                  95

Ala Glu Asp Val Gln Ile Asp Ala Trp Glu Thr Ile Gly Asn Thr Gly
            100                 105                 110

Trp Thr Trp Lys Asn Leu Phe Pro Tyr Tyr Arg Lys Ser Glu Asn Phe
        115                 120                 125

Thr Val Pro Thr Lys Ser Gln Thr Ser Leu Gly Ala Ser Tyr Glu Ala
    130                 135                 140

Gly Ala His Gly His Glu Gly Pro Leu Asp Val Ala Phe Thr Gln Ile
145                 150                 155                 160

Glu Ser Asn Asn Leu Thr Thr Tyr Leu Asn Arg Thr Phe Gln Gly Met
                165                 170                 175

Gly Leu Pro Trp Thr Glu Asp Val Asn Gly Gly Lys Met Arg Gly Phe
            180                 185                 190

Asn Leu Tyr Pro Ser Thr Val Asn Leu Glu Glu Tyr Val Arg Glu Asp
        195                 200                 205

Ala Ala Arg Ala Tyr Tyr Trp Pro Tyr Lys Ser Arg Pro Asn Leu His
    210                 215                 220

Val Leu Leu Asn Thr Phe Ala Asn Arg Ile Val Trp Asp Gly Glu Ala
225                 230                 235                 240
```

```
Arg Asp Gly Asp Ile Thr Ala Ser Gly Val Glu Ile Thr Ser Arg Asn
                245                 250                 255

Gly Thr Val Arg Val Ile Asn Ala Glu Lys Glu Val Ile Val Ser Ala
            260                 265                 270

Gly Ala Leu Lys Ser Pro Ala Ile Leu Glu Leu Ser Gly Ile Gly Asn
        275                 280                 285

Pro Ser Val Leu Asp Lys Tyr Asn Ile Pro Val Lys Val Asn Leu Pro
    290                 295                 300

Thr Val Gly Glu Asn Leu Gln Asp Gln Val Asn Ser His Met Asp Ala
305                 310                 315                 320

Ser Gly Asn Thr Ser Ile Ser Gly Thr Lys Ala Val Ser Tyr Pro Asp
                325                 330                 335

Val Tyr Asp Val Phe Gly Asp Glu Ala Glu Ser Val Ala Lys Gln Ile
            340                 345                 350

Arg Ala Ser Leu Lys Gln Tyr Ala Ala Asp Thr Ala Gln Ala Asn Gly
        355                 360                 365

Asn Ile Met Lys Ala Ala Asp Leu Glu Arg Leu Phe Glu Val Gln Tyr
    370                 375                 380

Asp Leu Ile Phe Lys Gly Arg Val Pro Ile Ala Glu Val Leu Asn Tyr
385                 390                 395                 400

Pro Gly Ser Ala Thr Ser Val Phe Ala Glu Phe Trp Ala Leu Leu Pro
                405                 410                 415

Phe Ala Arg Gly Ser Val His Ile Gly Ser Ser Asn Pro Val Glu Phe
            420                 425                 430

Pro Val Ile Asn Pro Asn Tyr Phe Met Leu Asp Trp Asp Ala Lys Ser
        435                 440                 445

Tyr Val Ala Val Ala Lys Tyr Ile Arg Arg Ser Phe Glu Ser Tyr Pro
    450                 455                 460

Leu Ser Ser Ile Val Lys Glu Ser Thr Pro Gly Tyr Asp Val Ile Pro
465                 470                 475                 480

Arg Asn Ala Ser Glu Gln Ser Trp Lys Glu Trp Val Phe Asp Lys Asn
                485                 490                 495

Tyr Arg Ser Asn Phe His Pro Val Gly Thr Ala Ala Met Met Pro Arg
            500                 505                 510

Glu Ile Gly Gly Val Val Asp Glu Arg Leu Asn Val Tyr Gly Thr Thr
        515                 520                 525

Asn Val Arg Val Val Asp Ala Ser Val Leu Pro Phe Gln Val Cys Gly
    530                 535                 540

His Leu Val Ser Thr Leu Tyr Ala Val Ala Glu Arg Ala Ala Asp Leu
545                 550                 555                 560

Ile Lys Ala Asp Ala Gly Arg Arg
                565

<210> SEQ ID NO 13
<211> LENGTH: 36
<212> TYPE: DNA
<213> ORGANISM: Artificial Sequence
<220> FEATURE:
<223> OTHER INFORMATION: The sequence of designed polynucleotide
      described in Example 1

<400> SEQUENCE: 13
ggaattccat atgaaatatg attatatcgt tattgg                          36

<210> SEQ ID NO 14
<211> LENGTH: 32
```

```
<212> TYPE: DNA
<213> ORGANISM: Artificial Sequence
<220> FEATURE:
<223> OTHER INFORMATION: The sequence of designed polynucleotide
      described in Example 1

<400> SEQUENCE: 14
cgggatccga agcgatgagt ataggtacct tc                                       32

<210> SEQ ID NO 15
<211> LENGTH: 14
<212> TYPE: PRT
<213> ORGANISM: Artificial Sequence
<220> FEATURE:
<223> OTHER INFORMATION: The sequence of peptide fragment described in
      experimental example 1

<400> SEQUENCE: 15

Ile Gly Gly Val Val Asp Thr Ser Leu Lys Val Tyr Gly Thr
1               5                   10

<210> SEQ ID NO 16
<211> LENGTH: 20
<212> TYPE: PRT
<213> ORGANISM: Artificial Sequence
<220> FEATURE:
<223> OTHER INFORMATION: The sequence of peptide fragment described in
      experimental example 1

<400> SEQUENCE: 16

Trp Gly Gly Gly Thr Lys Gln Thr Val Arg Ala Gly Lys Ala Leu Gly
1               5                   10                  15

Gly Thr Ser Thr
            20

<210> SEQ ID NO 17
<211> LENGTH: 25
<212> TYPE: PRT
<213> ORGANISM: Artificial Sequence
<220> FEATURE:
<223> OTHER INFORMATION: The sequence of peptide fragment described in
      experimental example 1

<400> SEQUENCE: 17

Met Leu Gly Lys Leu Ser Phe Leu Ser Ala Leu Ser Leu Ala Val Ala
1               5                   10                  15

Ala Thr Leu Ser Asn Ser Thr Ser Ala
            20                  25

<210> SEQ ID NO 18
<211> LENGTH: 22
<212> TYPE: PRT
<213> ORGANISM: Aspergillus oryzae

<400> SEQUENCE: 18

Met Leu Phe Ser Leu Ala Phe Leu Ser Ala Leu Ser Leu Ala Thr Ala
1               5                   10                  15

Ser Pro Ala Gly Arg Ala
            20
```

METHOD FOR HIGHLY EXPRESSING RECOMBINANT GLUCOSE DEHYDROGENASE DERIVED FROM FILAMENTOUS FUNGI

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: 32,371 bytes ASCII (Text) file named "701380RevisedSequenceListing.txt," created Oct. 10, 2008.

TECHNICAL FIELD

The present invention relates to a method for highly expressing recombinant glucose dehydrogenase derived from filamentous fungi.

BACKGROUND ART

Self-monitoring of blood glucose is important for a patient with diabetes to figure out a usual blood glucose level in the patient and apply it to treatment. An enzyme taking glucose as a substrate is utilized for a sensor used for the self-monitoring of blood glucose. An example of such an enzyme includes, for example, glucose oxidase (EC. 1.1.3.4). Glucose oxidase is advantageous in that it has high specificity for glucose and is excellent in thermal stability, and thus has been used as the enzyme for a blood glucose sensor from a long time ago. Its first publication goes back 40 years ago. In the blood glucose sensor using glucose oxidase, the measurement is performed by transferring electrons produced in a process of oxidizing glucose to convert into D-glucono-δ-lactone to an electrode via a mediator. However, glucose oxidase easily transfers protons produced in the reaction to oxygen, and thus dissolved oxygen affects the measured value, which has been problematic.

In order to avoid such a problem, for example, NAD(P)-dependent glucose dehydrogenase (EC. 1.1.1.47) or pyrrolo-quinoline quinone-dependent glucose dehydrogenase (EC. 1.1.5.2; former EC. 1.1.99.17) is used as the enzyme for the blood glucose sensor. They dominates in that they are not affected by dissolved oxygen, but the former NAD(P)-dependent glucose dehydrogenase has the poor stability and requires the addition of the coenzyme. Meanwhile, the latter pyrrolo-quinoline quinone-dependent glucose dehydrogenase is inferior in substrate specificity, reacts with other sugars such as maltose and lactose and thus correctness of the measured value is impaired.

In Non-patent documents 1 to 4, glucose dehydrogenase derived from *Aspergillus oryzae* has been reported, but no glucose dehydrogenase gene has been reported. In Non-patent documents 1 to 4, it has not been described to produce the glucose dehydrogenase derived from *Aspergillus oryzae* by gene recombination.

Non-patent literature 1: Biochim. Biophys. Acta., Jul. 11, 1967; 139 (2):265-76
Non-patent literature 2: Biochim. Biophys. Acta., Jul. 11, 1967; 139 (2):277-93
Non-patent literature 3: Biochim Biophys Acta. 146(2):317-27
Non-patent literature 4: Biochim Biophys Acta. 146(2):328-35

In Patent document 1, flavin-binding type glucose dehydrogenase derived from genus *Aspergillus* has been disclosed. This enzyme dominates in that this is excellent in substrate specificity and is not affected by the dissolved oxygen. For the thermal stability, it has been described that a residual activity ratio after being treated at 50° C. for 15 minutes is about 89% and this enzyme is excellent in thermal stability (hereinafter also described as heat resistance). In Patent document 2, a gene sequence and an amino acid sequence of that enzyme have been reported.

Patent document 1: WO2004/058958
Patent document 2: WO2006/101239

However, it is very difficult even using recombinant DNA technology to produce flavin-binding type glucose dehydrogenase (also referred to as FAD-dependent glucose dehydrogenase). In fact, a yield of FAD-dependent glucose dehydrogenase in recombinant *Escherichia coli* K-12 strain disclosed in Patent document 2 was 0.09 U/mL, which was an extremely low level. The *Escherichia coli* K-12 strain is most commonly used in recombinant protein production, and is a host most frequently used industrially in terms of easy recombinant engineering, easy culture and safety. Therefore, a method for efficiently producing recombinant FAD-dependent glucose dehydrogenase using the *Escherichia coli* K-12 strain as the host has been desired.

DISCLOSURE OF THE INVENTION

It is an object of the present invention to provide an enzyme for the blood glucose sensor which is practically more advantageous. More specifically, glucose dehydrogenase (GDH) derived from filamentous fungi, which is excellent in not only substrate specificity but also production cost is acquired and utilized on a large scale.

For accomplishing the above objects, the present inventors specified and acquired a glucose dehydrogenase gene derived from *Aspergillus oryzae* by utilizing genomic information of *Aspergillus oryzae* and found that glucose dehydrogenase derived from *Aspergillus oryzae* could be acquired from *Escherichia coli* using the gene. They also deduced an amino acid sequence from genomic information, and found that an amino acid sequence thought to be a signal peptide was present in an N-terminal region of the amino acid sequence.

Since the signal peptide acts as a migration signal to a periplasma space, a potential restriction to an amount of a protein to be expressed was concerned because of a capacity of the space. Thus, a function of the signal peptide was deleted. Consequently, the productivity of GDH was increased by about 10 times, and it became possible to reduce the production cost to 1/10.

Thus, the invention comprises the following.

[1] A method for producing recombinant glucose dehydrogenase (hereinafter sometimes abbreviated as GDH) derived from filamentous fungus characterized in that one or more mutation is introduced in a signal peptide sequence present in an N terminal region of GDH, thereby increasing an amount of expressed GDH compared with an amount before introduction of the mutation.

[2] The method for producing recombinant GDH derived from filamentous fungus according to [1] characterized in that a part of an amino acid sequence of the signal peptide present in the N-terminal region of GDH is deleted or substituted, thereby increasing the amount of expressed GDH compared with the amount before the introduction of the mutation.

3. The method for producing GDH according to claim 1 characterized in that a part or all of an amino acid sequence, MLFSLAFLSALSLATASPAGRA (SEQ ID NO: 18), present in an N terminal region in the amino acid sequence described in SEQ ID NO: 2 or 4 is deleted and expressed, thereby increasing the expressed amount compared with a case where this amino acid sequence is present.

4. The method for producing GDH according to claim 1 characterized in that 1 to 22 amino acid residues are substituted or inserted in an amino acid sequence MLFSLAFLSALSLATASPAGRA (SEQ ID NO: 18) present in the N terminal region in the amino acid sequence described in SEQ ID NO: 2 or 4, thereby increasing an expression activity compared with a case where the original amino acid sequence is present.

5. The method for producing GDH according to claim 1 characterized in that by a part or all of an amino acid sequence MLGKLSFLSALSLAVAATLSNSTSA (SEQ ID NO: 17) present in the N terminal region of glucose dehydrogenase derived from filamentous fungus is deleted and expressed, thereby increasing the expressed amount compared with a case where this amino acid sequence is present, or 1 to 25 amino acid residues are substituted or inserted, thereby increasing an expression activity compared with a case where the original amino acid sequence is present.

[6] A DNA sequence which encodes a GDH gene substituting and/or deleting a part or all of a DNA sequence encoding a signal peptide present in an N terminal region of glucose dehydrogenase (GDH) derived from filamentous fungus, and is used for the method of any of [1] to [5].

[7] A recombinant vector comprising the DNA sequence of [6].

[8] A transformant introducing the recombinant vector according to [7] into a host.

[9] A GDH protein produced using the transformant according to [8].

[10] A composition comprising the GDH protein according to [9].

[11] A method for measuring a glucose concentration using the composition according to [10].

[12] A glucose sensor comprising the composition according to [11].

According to the present invention, it has become possible to efficiently produce glucose dehydrogenase and obtain more practical glucose dehydrogenase.

According to the present invention, it has become possible to efficiently produce recombinant glucose dehydrogenase and obtain more practical glucose dehydrogenase in terms of industrial usage by deducing the amino acid sequence from the glucose dehydrogenase gene isolated from the microorganism belonging to genus *Aspergillus* or *Penicillium*, predicting the signal peptide region, deleting the DNA sequence encoding a part or all of the signal peptide, or substituting or inserting amino acid residues in the amino acid sequence encoding the signal peptide.

BRIEF DESCRIPTION OF THE DRAWINGS

FIG. 1 shows signal profiles predicting a cleavage site in a signal peptide in FAD-GDH derived from *Aspergillus oryzae*;

BEST MODES FOR CARRYING OUT THE INVENTION

Figure 2:
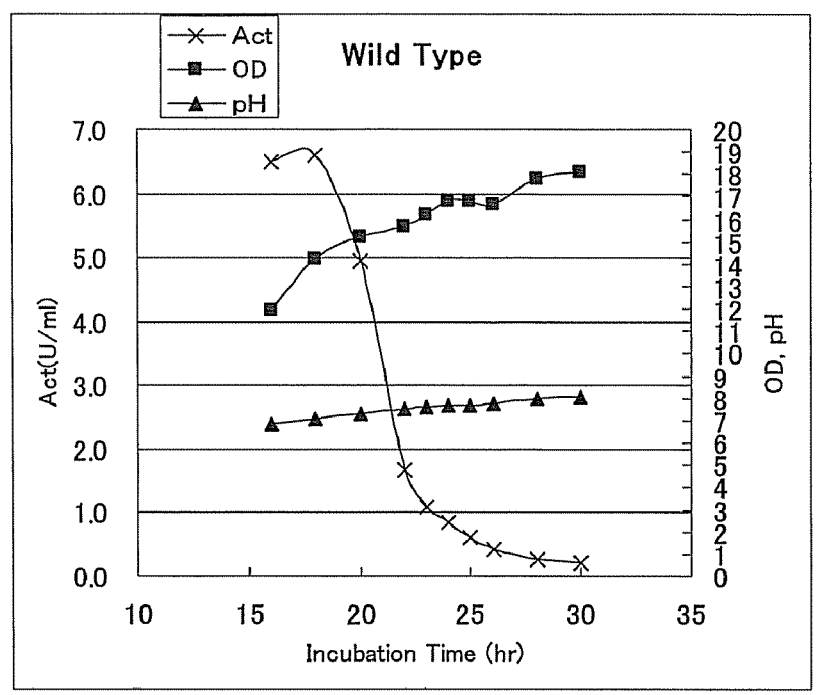
FIG. 2 is a graph showing the relation of a culture phase of GDH (having the signal peptide) derived from wild type *A. oryzae* with a turbidity (OD), pH and a GDH activity of microbial cells.

One embodiment of the present invention is the method for producing GDH characterized in that a mutation is introduced in a signal peptide sequence present in an N terminal region of GDH, thereby increasing an amount of expressed GDH compared with an amount before introduction of the mutation in the method for producing the recombinant GDH derived from the filamentous fungus.

As a result of an extensive study for acquiring a GDH protein in high yield, in order to accomplish the above object, the present inventors have first found the gene DNA predicted to encode glucose dehydrogenase as an original gene DNA for modification by utilizing the genomic information of *Aspergillus oryzae* in the previous invention.

The present inventors found the gene DNA predicted to encode FAD-dependent glucose dehydrogenase (hereinafter abbreviated as "GDH") by utilizing the NCBI database.

These recombinant GDH can be obtained as the water soluble fraction containing the GDH by yielding the gene encoding the GDH by PCR, inserting this gene into an expression vector, culturing a transformant obtained by transforming an appropriate host, collecting microbial cells from the culture medium by centrifugation, subsequently disrupting the microbial cells by the mechanical method or the enzymatic method using lysozyme and if necessary adding the chelating agent such as EDTA and the surfactant to solubilize. Alternatively, by the use of an appropriate host-vector system, it is possible to secret the expressed GDH directly in the medium.

In the present invention, it is possible to lower the function of the signal peptide by deleting or substituting a part of the amino acid sequence of the signal peptide present at the N terminal region of GDH.

For example, in the GDH having the amino acid sequence described in SEQ ID NO: 4, it is possible to lower the function of the signal peptide by deleting a part or all of the amino acid sequence MLFSLAFLSALSLATASPAGRA (SEQ ID NO: 18) present at its N terminus. Alternatively, it is also possible to lower the function of the signal peptide by substituting or/and inserting 1 to 22 amino acid residues.

As a specific position to be substituted, for example, a cleaved site in the signal peptide can be exemplified. Preferably, it is possible to lower the function by substituting alanine corresponding to the C terminus in the signal peptide with another amino acid.

Whether the expression amount of the objective enzyme has been enhanced or not compared with the state where the signal peptide sequence is present can be identified by comparing total activity values per 1 mL of the medium before and after introducing the mutation into the sequence. The modification of the signal peptide sequence can be confirmed by N terminal amino acid sequencing using Edman degradation.

It was found that the amount of the expressed GDH protein was increased by deleting the function of the signal peptide present in its N terminal region.

As the tool which predicts the signal peptide, PSORT and Signal P software have been frequently used. They are available from web address of psort.nibb.ac.jp/ and www.cbs.dtu.dk/services/SignalP-2.0/, respectively.

Using Signal P software, the cleavage site of the signal peptide was predicted in the amino acid sequence (SEQ ID NO:9) deduced from the GDH gene derived from *Aspergillus oryzae*. Consequently, it was predicted that the signal peptide was potentially cleaved between alanine at position 16 and serine at position 17 or between alanine at position 22 and lysine at position 23 (FIG. 1).

For example, the above GDH gene derived from *Aspergillus oryzae* is inserted into an expression vector (many vectors such as plasmids are known in the art), and an appropriate host (many hosts such as *Escherichia coli* are known in the art) is transformed with the expression vector. A water soluble fraction containing GDH can be yielded by culturing the resulting transformant, collecting microbial cells from the medium by centrifugation, disrupting the microbial cells by a mechanical method or an enzymatic method, e.g., using lysozyme and if necessary adding a chelating agent such as EDTA and a surfactant to solubilize. Alternatively, by the use of an appropriate host-vector system, it is possible to secret the expressed GDH directly in the medium.

A GDH containing solution obtained as the above could be precipitated by concentration under reduced pressure, membrane concentration, salting out treatment using ammonium sulfate or sodium sulfate or fractional precipitation using a hydrophilic organic solvent such as methanol, ethanol or acetone. The treatment with heat and isoelectric focusing treatment are also effective purification procedures. The purified GDH can also be yielded by performing gel filtration using an absorbing agent or a gel filtration agent, absorption chromatography, ion exchange chromatography and affinity chromatography. It is preferable that the purified enzyme preparation is purified to an extent that the enzyme is detected as a single band on electrophoresis (SDS-PAGE).

These can be carried forward in accordance with the following references.

(a) Tanpakushitsu Jikken Protocol Vol. 1, Functional Analysis Vol. 2, Structural Analysis (Shujunsha) edited by Yoshifumi Nishimura and Shigeo Ohno.

(b) Revised Tanpakushitsu Jikken Note, Extraction and Separation/Purification (Yodosha) edited by Masato Okada and Kaori Miyazaki.

(c) Tanpakushitsu Jikken no Susumekata edited by Masato Okada and Kaori Miyazaki.

Alternatively, the above procedure can be carried forward by the methods exemplified below.

The present invention further includes a vector comprising the gene encoding GDH and a transformant transformed with the vector.

The produced DNA having the genetic information of the protein is transferred into the host microorganism by ligating to the vector, which becomes the transformant which produces the modified protein.

When the plasmid is used as the vector, pBluescript, pUC18 and the like can be used when *Escherichia coli* is used as the host microorganism. As the host microorganism, for example, *Escherichia coli* W3110, *Escherichia coli* C600, *Escherichia coli* JM109, *Escherichia coli* DH5α and the like can be utilized. As the method for transferring the recombinant vector into the host microorganism, it is possible to employ the method of transferring the recombinant DNA in the presence of calcium ions when the host microorganism is the microorganism belonging to genus *Escherichia*, and further, the electroporation method may be used. Furthermore, commercially available competent cells (e.g., Competent High DH5α supplied from Toyobo Co., Ltd.) may also be used.

Such a gene may be extracted from the fungal strain, or can also be synthesized chemically. Furthermore, it is also possible to yield a DNA fragment containing the GDH gene by the use of PCR.

In the present invention, the method for yielding the gene encoding GDH derived from the filamentous fungus includes the following methods. First, with reference to the sequence information of the GDH gene derived from *Aspergillus oryzae*, a predicted objective gene from filamentous fungus can be acquired. mRNA is prepared from the filamentous fungus and cDNA is synthesized. The GDH gene is amplified by PCR with the cDNA yielded in this way as the template, and the recombinant vector is constructed by binding and closing this gene and the vector at blunt ends or sticky ends of both DNA with DNA ligase. The recombinant vector is transferred into the host microorganism in which the vector can replicate, and subsequently, the microorganism carrying the recombinant vector containing the gene encoding GDH is yielded by utilizing a marker of the vector.

The base sequence of the GDH gene was decoded by a dideoxy method described in Science 214:1205, 1981. The amino acid sequence of GDH was deduced from the base sequence determined as the above.

As in the above, the once selected GDH gene in the recombinant vector can be easily transferred into another recombinant vector which can replicate in another microorganism by collecting the DNA which is the GDH gene from the recombinant vector carrying the GDH gene by restriction enzymes and PCR method and binding the DNA to another vector fragment. For the transformation of another microorganism with these vectors, the competent cell method by treating with calcium, the electroporation method and the protoplast method can be used.

The GDH gene of the present invention may be those having the DNA sequence so that a part of amino acid residues is deleted or substituted in the amino acid sequence after translation of the gene or so that other amino acid residues are added or substituted, as long as the protein encoded by the GDH gene has the glucose dehydrogenase activity.

As the method for modifying the gene encoding the wild type GDH, the typically performed technique to modify the genetic information is used. That is, DNA having the genetic information of the modified protein is made by converting the specific base in DNA having the genetic information of the protein or inserting or deleting the specific base. The specific methods for converting the base in the DNA include the use of commercially available kits (Transformer Mutagenesis Kit supplied from Clonetech; EXQIII/Mung Bean Deletion Kit supplied from Stratagene; QuickChange Site Directed Mutagenesis Kit supplied from Stratagene), or utilization of polymerase chain reaction (PCR) method.

For the culture of the host microorganism which is the transformant, a culture condition could be selected in consideration of nutritional physiological natures of the host. It is advantageous that the transformant is cultured in liquid culture in many cases and industrially ventilation stirring culture is performed.

As nutrient sources of the medium, those typically used for the culture of the microorganism can be widely used. Carbon sources may be carbon compounds capable of being assimilated. For example, glucose, sucrose, lactose, maltose, lactose, molasses and pyruvic acid are used. Nitrogen sources may be usable nitrogen compounds. For example, peptone, meat extracts, yeast extracts, casein hydrolyzed products, and bean cake extracted with alkali are used. In addition, phosphate salts, carbonate salts, sulfate salts, salts of magnesium, calcium, potassium, iron, manganese and zinc, particular amino acids and particular vitamins are used if necessary.

A culture temperature can be appropriately changed in the range in which the microorganism grows and produces GDH, and is preferably about 20 to 37° C. A culture time period is somewhat different depending on the condition, the culture could be terminated at an appropriate time period by judging the time to be right to reach the maximum yield of GDH, and the culture time period is typically about 6 to 48 hours.

In the culture of the recombinant GDH derived from the filamentous fungus, it is particularly important to control pH in the medium. It is desirable to control to pH 7.1 to 7.3 or lower, and it is particularly preferable to culture with controlling in the range of pH 6.0 to 7.3. By culturing with controlling pH in this way, it becomes possible to prepare the GDH protein derived from the filamentous fungus in a large amount.

However, GDH derived from the filamentous fungus keeps the high stability in an acidic region of pH 7.0 or lower, but becomes unstable at pH 7.1 to 7.3 or higher and its activity lowers rapidly.

Therefore, in the present invention, it is preferable to control pH to 7.3 or lower in the culture in the production of the recombinant glucose dehydrogenase (GDH) derived from the filamentous fungus.

In the production by culturing the recombinant GDH derived from the filamentous fungus, when the pH value was increased by 0.2, the activity was decreased by 10% or more compared with the original activity, and the activity was decreased by about 30% at the maximum depending on GDH. Thus, in the present patent, an efficacy to control pH to the level or lower of pH (specifically pH of 7.3 or less, preferably 7.1 or less) in the culture medium before lowering the activity in a phenomenon that the activity was decreased by 10% or more when the pH value was increased by 0.2 was presumed, and actually examined and confirmed.

In the culture of the recombinant organism, it is generally performed to control the pH value because death of microbial cells and degradation of the objective protein are concerned, and it is common to usually keep the pH vale in the neutral region. There is no example to describe the necessity to keep the pH value neutral or lower as this case of glucose dehydrogenase derived from the filamentous fungus.

The culture medium containing the microbial cells which produce GDH can be directly collected and utilized. However, in general, according to standard methods, when the GDH is present in the culture medium, a GDH-containing solution is separated from the microorganism microbial cells by filtration or centrifugation, and subsequently utilized. When GDH is present in the microbial cells, the microbial cells are collected from the culture by filtration or centrifugation, then disrupted by the mechanical method or the enzymatic method using lysozyme and if necessary the chelating agent such as EDTA and the surfactant are added to solubilize, and GDH is separated/collected as an aqueous solution.

The GDH-containing solution obtained as the above could be precipitated by concentration under reduced pressure, membrane concentration, salting out treatment using ammonium sulfate or sodium sulfate or fractional precipitation using the hydrophilic organic solvent such as methanol, ethanol or acetone. The treatment with heat and isoelectric focusing treatment are also effective purification procedures. The purified GDH can also be yielded by subsequently performing gel filtration using the absorbing agent or the gel filtration agent, absorption chromatography, ion exchange chromatography and affinity chromatography.

For example, it is possible to obtain a purified enzyme preparation by separating and purifying by gel filtration using Sephadex gel (supplied from GE Health Care Bioscience), or column chromatography using DEAE Sepharose CL-6B (supplied from GE Health Care Bioscience) or Octyl Sepharose CL-6B (supplied from GE Health Care Bioscience). It is preferable that the purified enzyme preparation is purified to the extent that the enzyme is detected as a single band on electrophoresis (SDS-PAGE).

Test Example

In the present invention, the glucose dehydrogenase activity is measured under the following condition.

<Reagents>

50 mM PIPES buffer pH 6.5 (including 0.1% Triton X-100) 14 mM 2,6-dichlorophenol-indophenol (DCPIP) solution 1 M D-glucose solution.

A reaction reagent is made by mixing 15.8 mL of the PIPES buffer, 0.2 mL of the DCPIP solution and 4 mL of the D-glucose solution.

<Measurement Condition>

The reaction reagent (2.9 mL) is preliminarily heated at 37° C. for 5 minutes. The GDH solution (0.1 mL) is added and gently mixed, subsequently the change of absorbance at 600 nm is recorded for 5 minutes using a spectrophotometer controlled to 37° C. using water as a control, and the change of absorbance per one minute ($\Delta OD_{TEST}$) is calculated from a linear portion of the record. The solvent in which GDH will be dissolved in place of the blinded GDH solution is added to the reagent mixture, and the change of absorbance ($\Delta OD_{BLANK}$) per one minute is measured. The GDH activity is calculated from these values according to the following formula. One unit (U) in the GDH activity is defined as the amount of the enzyme which reduces 1 μM DCPIP for one minute in the presence of 200 mM D-glucose.

Activity (U/mL)=[−(ΔOD$_{TEST}$−ΔOD$_{BLANK}$)×3.0× dilution scale]/(16.3×0.1×1.0)

In the above formula, 3.0 represents a liquid amount (mL) of the reaction reagent+the enzyme solution, 16.3 represents a millimolar molecular absorbance coefficient (cm$^2$/μmol) in the condition of measuring the present activity, 0.1 represents the liquid amount of the enzyme solution (mL) and 1.0 represents a light path length (cm) of the cell.

EXAMPLES

The present invention will be more specifically described below by Examples, but the present invention is not limited to the following Examples.

DNA (gene) composed of the base sequence described in SEQ ID NO:1 is the DNA comprising DNA (gene) encoding glucose dehydrogenase derived from *Aspergillus oryzae* RIB40 strain, predicted from the database of NCBI and removing the intron from the genomic gene sequence including the intron. SEQ ID NO:2 represents the amino acid sequence corresponding thereto.

The gene encoding the protein composed of the amino acid sequence described in SEQ ID NO:2 indicates the full sequence of the glucose dehydrogenase gene predicted from the database of NCBI.

The DNA (gene) composed of the base sequence described in SEQ ID NO:3 indicates the full sequence of the DNA (gene) encoding the protein having the glucose dehydrogenase activity derived from *Aspergillus oryzae* TI strain described later and identified by the present inventor. SEQ ID NO: 4 represents the amino acid sequence corresponding thereto.

The DNA (gene) which hybridizes with the DNA composed of the base sequence complementary to the base sequence described in SEQ ID NO:3 under the stringent condition and encodes the protein having the glucose dehydrogenase activity is included in the applicable scope of the present invention.

The gene encoding the protein composed of the amino acid sequence described in SEQ ID NO:4 indicates the full sequence of the DNA (gene) encoding the protein having the glucose dehydrogenase activity derived from *Aspergillus oryzae* TI strain described later.

The DNA (gene) encoding the protein composed of the amino acid sequence having one or more amino acid deletions, substitutions or additions (insertions) in the amino acid sequence described in SEQ ID NO:4 and having the glucose dehydrogenase activity is included in the applicable scope of the present invention.

An outline of the procedure to acquire the GDH gene derived from *Aspergillus oryzae* described in Examples shown below is as follows.

In order to acquire the GDH gene derived from *Aspergillus oryzae*, the purification of GDH from the culture supernatant of *Aspergillus oryzae* and *Aspergillus terreus* was tried using salting out, chromatography and the like, but it was difficult to yield GDH with high purity (Experiment 1 [1])

Therefore, we had no choice but to give up the cloning utilizing the partial amino acid sequence, which was one of standard methods to acquire the gene.

Thus, we searched GDH-producing microorganisms other than the above microorganisms, and as a result of an extensive study, we found that *Penicillium lilacinoechinulatum* NBRC6231 produced GDH, and succeeded to yield the purified enzyme with high purity from the culture medium of this fungal strain (Experiment 1 [2]).

Subsequently, we succeeded to determine the partial amino acid sequence using the above enzyme, partially acquired the GDH gene derived from *P. lilacinoechinulatum* NBRC6231 by PCR based on the determined amino acid sequence and determined its base sequence (1356 bp) (Experiment 1 [3] and [4]).

Finally, based on this base sequence, the GDH gene derived from *Aspergillus oryzae* was presumed (Experiment 1 [5]) from the published database of *Aspergillus oryzae* genome, and it was acquired.

<Experiment 1>

Estimation of Glucose Dehydrogenase Gene Derived from *Aspergillus oryzae*

[1] Acquisition of GDH Derived from *Aspergillus oryzae* (Hereinafter Sometimes Referred to as "AOGDH")

*Aspergillus oryzae* obtained from soils and stored as dried microbial cells according to standard methods was used. This is referred to as *Aspergillus oryzae* TI strain below.

*Aspergillus oryzae* TI strain was restored by inoculating its dry microbial cells in the potato dextrose agar medium (supplied from Difco) and incubating at 25° C. Fungal threads restored on the plate were collected including the agar, which was then suspended in filtrated sterilized water. In two 10 L jar fermenters 6 L of a production medium (1% malt extract, 1.5% soy bean peptide, 0.1% MgSO4(7H2O, 2% glucose, pH 6.5) was prepared and sterilized by autoclave at 120(C for 15 minutes. After cooling, the above fungal thread suspension was inoculated, and cultured with ventilation and stirring at 30 (C. The culture was stopped 64 hours after the start of the culture, and a filtrate containing the GDH activity was collected by removing the fungal threads by filtration. Low molecular substances were removed from the collected supernatant by ultrafiltration (molecular weight 10,000 cut off). Then, ammonium sulfate was added at 60% saturation to perform ammonium sulfate fractionation. The supernatant containing the GDH activity was collected by centrifugation, absorbed to the Octyl-Sepharose column, and eluted with ammonium sulfate having the gradient from 60% saturation to 0% to collect fractions having the GDH activity. The resulting GDH solution was applied onto the G-25 Sepharose column to perform the salting out. Ammonium sulfate was added at 60% saturation thereto. The mixture was absorbed to the Phenyl-Sepharose column and eluted with ammonium sulfate having the gradient from 60% saturation to 0% to collect fractions having the GDH activity. The fraction having the GDH activity was heated at 50(C for 45 minutes, and then centrifuged to yield the supernatant. The solution obtained from the above steps was made a purified GDH preparation (AOGDH). In the above purification process, 20 mM potassium phosphate buffer (pH 6.5) was used as the buffer. In order to determine the partial amino acid sequence of the AOGDH, the further purification was tried using various procedures such as ion exchange chromatography and gel filtration chromatography, but no purified preparation capable of being subjected to the partial amino acid sequencing could be obtained.

Also, we independently searched and obtained the microorganism belonging to *Aspergillus terreus*, and likewise tried the purification from its culture supernatant by the salting out and the Octyl-Sepharose, but no purified preparation capable of being subjected to the partial amino acid sequencing could be obtained as was the case with *Aspergillus oryzae*. Typically, using the purification methods commonly used, it is possible to obtain the protein preparation with high purity detected as a clear single band on SDS-PAGE. However, the GDH preparation at such a level could not be obtained. It was speculated that one of its causes was the sugar chain thought to be bound to the enzyme protein. Therefore, we had no choice but to give up the cloning utilizing the partial amino acid sequence of the protein, which was one of standard methods to acquire the gene.

[2] Acquisition of GDH Derived from Filamentous Fungus Belonging to Genus *Penicillium*

A purified preparation detected to be nearly uniform on SDS electrophoresis was acquired by using *Penicillium lilacinoechinulatum* NBRC6231 as the GDH producing fungus derived from the filamentous fungus belonging to genus *Penicillium* and performing the culture and the purification according to the same procedure as in the case with the above *Aspergillus oryzae*.

[3] Preparation of cDNA

For *Penicillium lilacinoechinulatum* NBRC6231, according to the above methods, the culture was carried out (but, the culture in the jar fermenter was performed for 24 hours), and the fungal threads were collected by filter paper filtration. The collected fungal threads were immediately frozen in liquid nitrogen, and disrupted using Cool Mill (supplied from Toyobo Co., Ltd.). The total RNA was immediately extracted from disrupted microbial cells using Sepasol RNA I (supplied from Nacalai Tesque) according to the protocol of this kit. mRNA was purified from the resulting total RNA using Origotex-dt30 (supplied from Daiichi Pure Chemicals Co., Ltd.), and RT-PCR with this as the template was performed using ReverTra-Plus™ supplied from Toyobo Co., Ltd. A resulting product was electrophoresed on agarose gel and a portion corresponding to a chain length of 0.5 to 4.0 kb was cut out. cDNA was extracted from a cut out gel fragment using MagExtractor-PCR&Gel Clean Up supplied from Toyobo Co., Ltd. and purified to use as a cDNA sample.

[4] Determination of GDH Gene Partial Sequence

The purified GDH derived from *Penicillium lilacinoechinulatum* NBRC6231 was dissolved in Tris-HCl buffer (pH 6.8) containing 0.1% SDS and 10% glycerol, and partially digested by adding Glu specific V8 endoprotease at a final concentration of 10 μg/mL thereto and incubating at 37(C for 16 hours. This sample was electrophoresed on 16% acrylamide gel to separate peptides. Peptide molecules present in this gel were transferred on a PVDF membrane using the buffer for blotting (1.4% glycine, 0.3% Tris and 20% ethanol) by semi-dry method. The peptides transferred onto the PVDF membrane were stained using a CBB staining kit (GelCode Blue Stain Reagent supplied from PIERCE), two band portions of the visualized peptide fragments were cut out and internal amino acid sequences were analyzed using a peptide sequencer. The resulting amino acid sequences were IGGVVDTSLKVYGT (SEQ ID NO:5) and WGGGTKQTVRAGKALGGTST (SEQ ID NO:6). Based on this sequence, degenerate primers containing mixed bases were made, and PCR was performed using the cDNA derived from NBRC6231 as the template. An amplified product was obtained, and was detected as a single band of about 1.4 kb by agarose gel electrophoresis. This band was cut out, and extracted and purified using MagExtractor-PCR&Gel Clean Up supplied from Toyobo Co., Ltd. The purified DNA fragment was TA-cloned using TArget Clone-Plus, and *Escherichia coli* JM 109 competent cells (Competent High JM109 supplied from Toyobo Co., Ltd.) were transformed with the resulting vector by heat shock. Among transformed clones, for colonies in which an insert had been identified by blue-white determination, the plasmid was extracted and purified using MagExtractor-Plasmid by miniprep, and the base sequence (1356 bp) of the insert was determined using plasmid sequence specific primers.

[5] Estimation of AOGDH Gene

Based on the determined base sequence, the homology was searched on the home page of "NCBI BLAST" (http://www.ncbi.nlm.nih.gov/BLAST/), and the AOGDH gene was estimated from multiple candidate sequences in consideration of the homology to publicly known glucose oxidation enzymes. The homology of the AOGDH estimated from the search to the GDH partial sequence derived from *P. lilacinoechinulatum* NBRC6231 was 49% at an amino acid level.

Example 1

Introduction of Glucose Dehydrogenase Gene Derived from *Aspergillus oryzae* (Hereinafter Sometimes Referred to as "AOGDH") into *Escherichia coli*

For the AOGDH gene, mRNA was prepared from *Aspergillus oryzae* microbial cells, and cDNA was synthesized. Two oligo DNA shown in SEQ ID NOS:5 and 6 were synthesized, and the AOGDH gene (wild type) was amplified using the prepared cDNA as the template and using KOD-Plus (supplied from Toyobo Co. Ltd.). The resulting DNA fragment was treated with NdeI and BamHI, and inserted into NdeI-BamHI sites in pBluescript (the NdeI site had been introduced to match a NdeI recognition sequence ATG to a translation initiation codon ATG of LacZ) to construct the recombinant plasmid. This plasmid was introduced into Competent High DH5α (supplied from Toyobo Co., Ltd.). The plasmid was extracted according to the standard method, and the base sequence of the AOGDH gene was determined (SEQ ID NO:3). The amino acid residues deduced from the DNA sequence were 593 amino acids (SEQ ID NO:4).

When FAD-GDH after cleaving the signal peptide was referred to as mFAD-GDH, the form in which only M had been added to the N terminus of mFAD-GDH and thus the N terminus of mFAD-GDH had been extended by one amino acid was expressed as S2. The form in which K at the N terminus of mFAD-GDH had been substituted with M and thus the total number of the amino acid residues was the same as mFAD-GDH was expressed as S3. For S2, PCR was performed using the oligonucleotide of SEQ ID NO:7 as the primer for the N terminal side and combining it with the primer of SEQ ID NO:6, and by the same procedure, the recombinant plasmid having the DNA sequence encoding S2 was constructed and the transformant was likewise acquired. For S3, PCR was performed using the oligonucleotide of SEQ ID NO:8 as the primer for the N terminal side and combining it with the primer of SEQ ID NO:6, and by the same procedure, the recombinant plasmid having the DNA sequence encoding S2 was constructed and the transformant was likewise acquired. It was confirmed by DNA sequencing that the plasmid having the DNA sequence for each modified FAD-GDH had no error in its sequence.

SEQ ID NO:9 represents the DNA sequence encoding the signal peptide-deleted mutant S2 determined above. SEQ ID NO:10 represents the amino acid sequence corresponding thereto.

Figure 3:
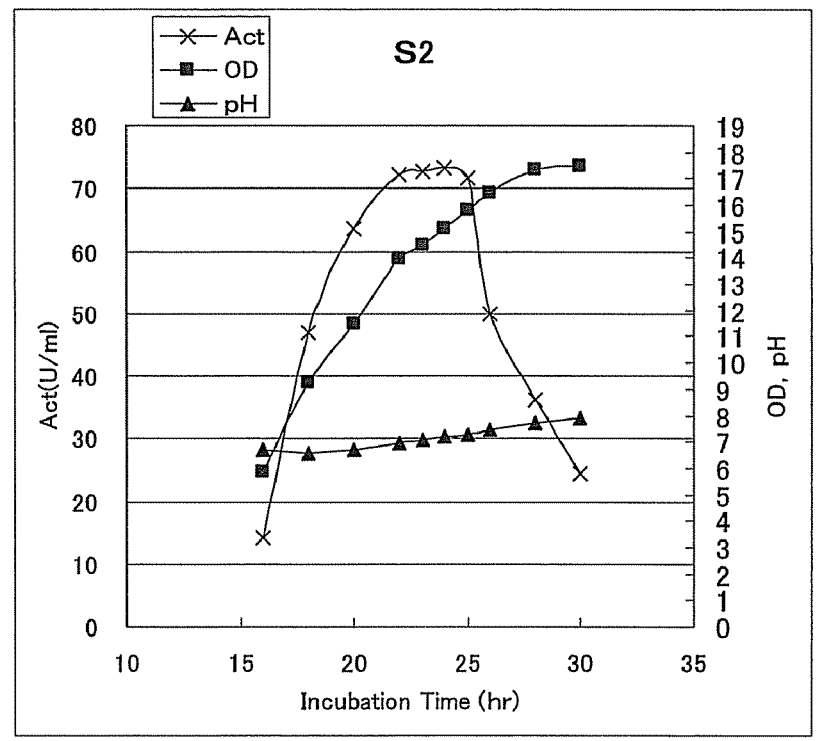
FIG. 3 is a graph showing the relation of the culture phase of GDH-S2 derived from mutant *A. oryzae* with the turbidity (OD), pH and the GDH activity of microbial cells.
Figure 4:
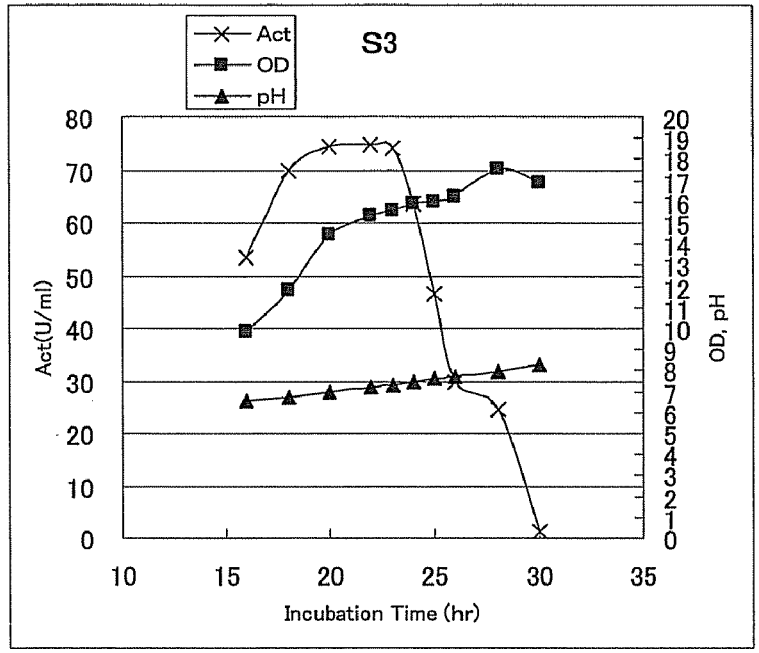
FIG. 4 is a graph showing the relation of the culture phase of GDH-S3 derived from mutant *A. oryzae* with the turbidity (OD), pH and the GDH activity of microbial cells.
Figure 5:
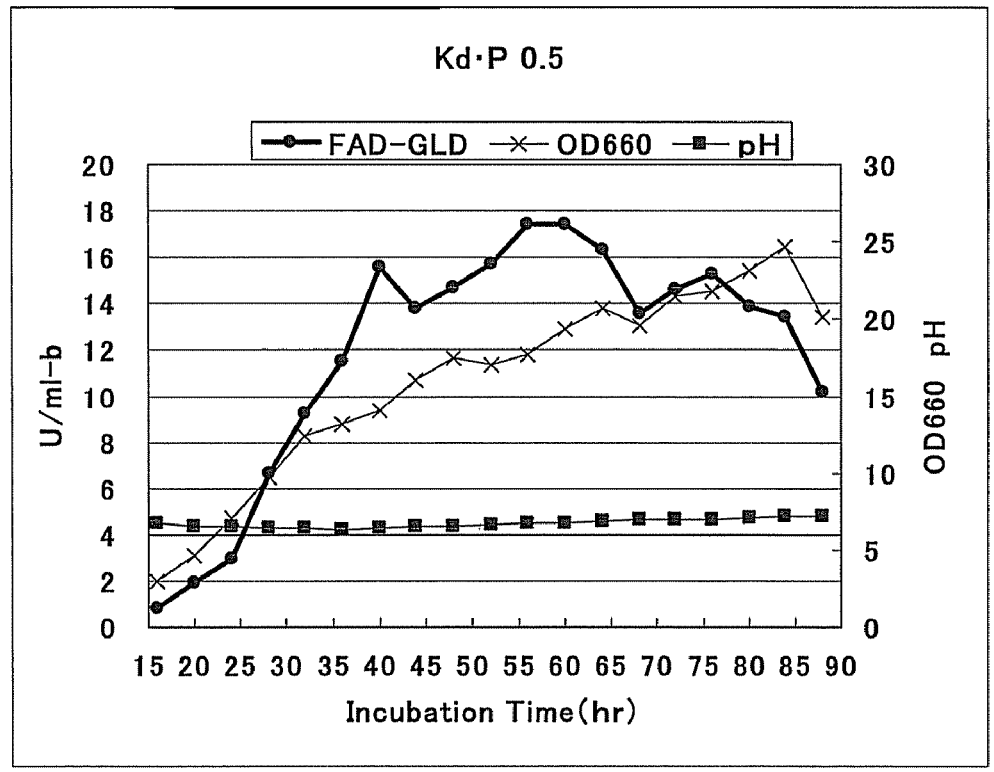
FIG. 5 is a graph showing the relation of the culture phase of GDH (the predicted signal peptide was removed) derived from wild type *A. terreus* at 28° C. at Kd•P of 0.5 with the turbidity (OD), pH and the GDH activity of microbial cells.
Figure 6:
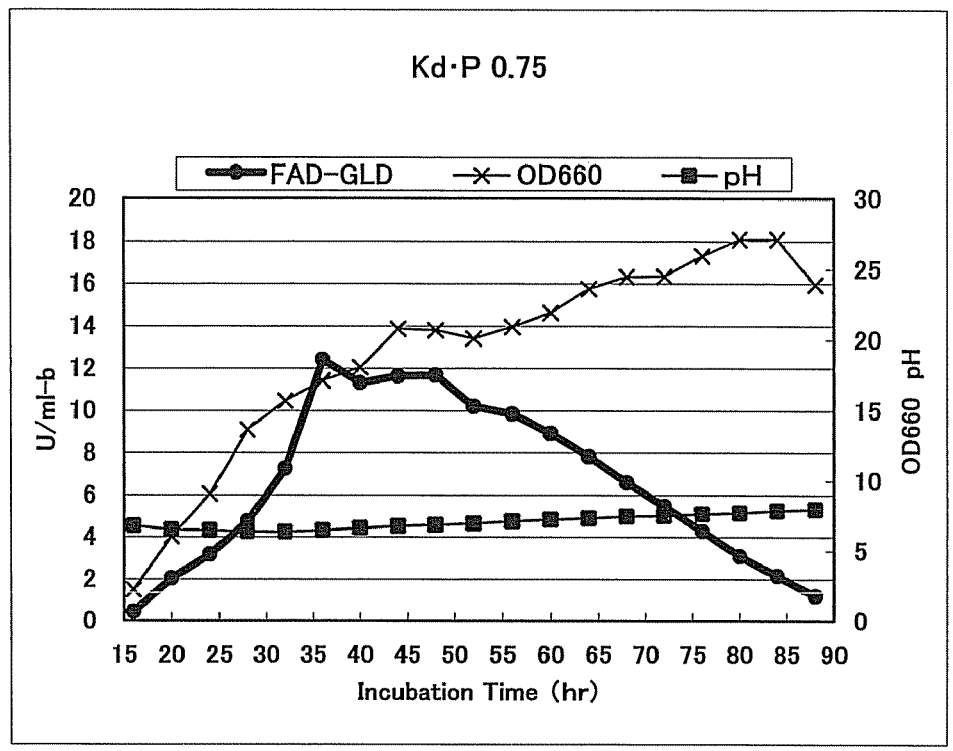
FIG. 6 is a graph showing the relation of the culture phase of GDH (the predicted signal peptide was removed) derived from wild type *A. terreus* at 28° C. at Kd•P of 0.75 with the turbidity (OD), pH and the GDH activity of microbial cells.
Figure 7:
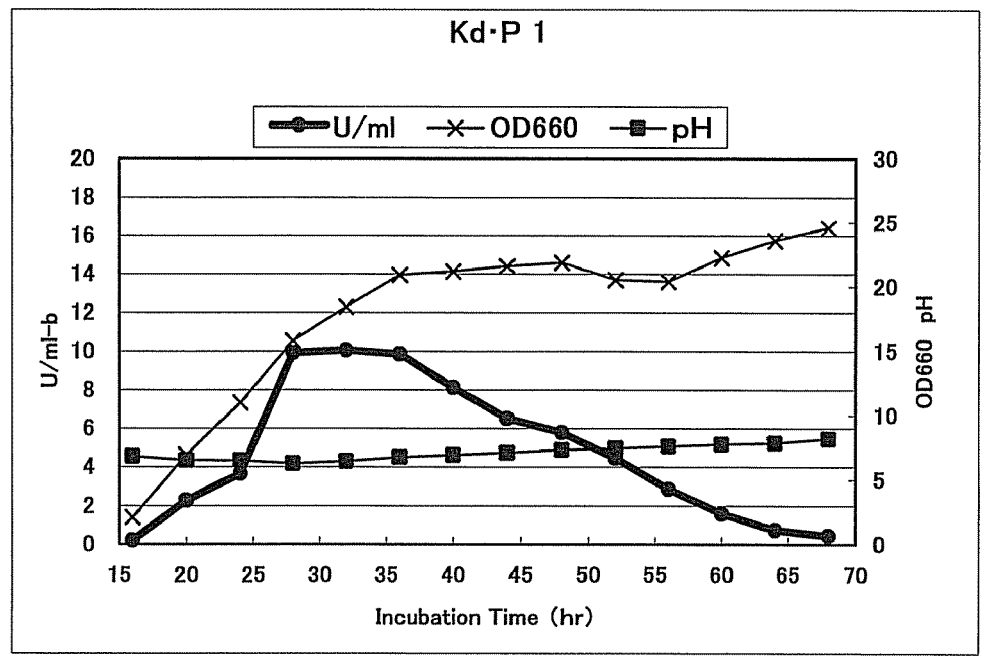
FIG. 7 is a graph showing the relation of the culture phase of GDH (the predicted signal peptide was removed) derived from wild type *A. terreus* at 28° C. at Kd•P of 1.0 with the turbidity (OD), pH and the GDH activity of microbial cells.
Figure 8:
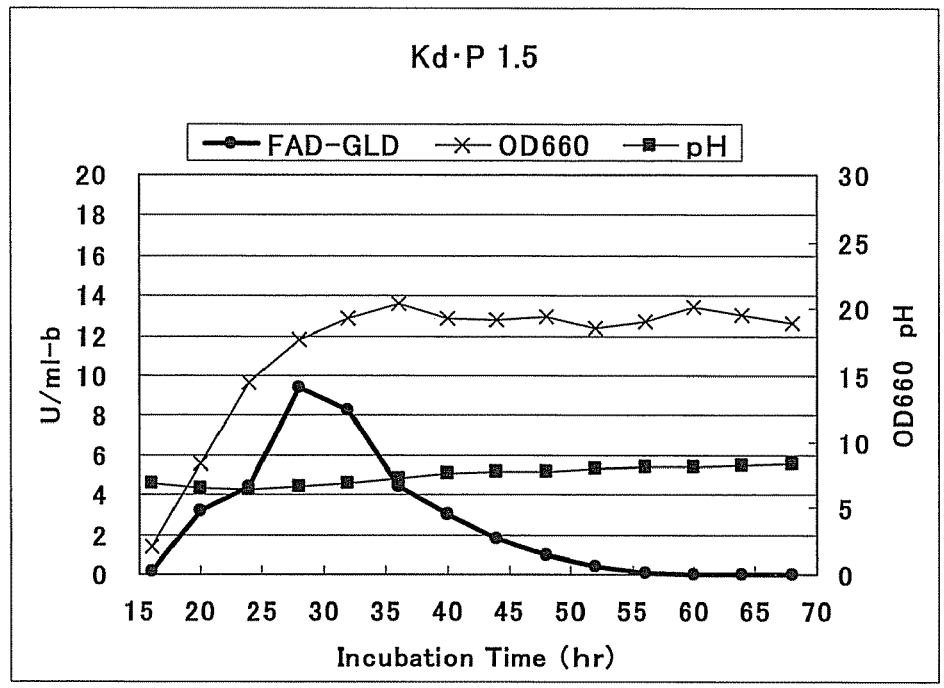
FIG. 8 is a graph showing the relation of the culture phase of GDH (the predicted signal peptide was removed) derived from wild type *A. terreus* at 28° C. at Kd•P of 1.5 with the turbidity (OD), pH and the GDH activity of microbial cells.
Figure 9:
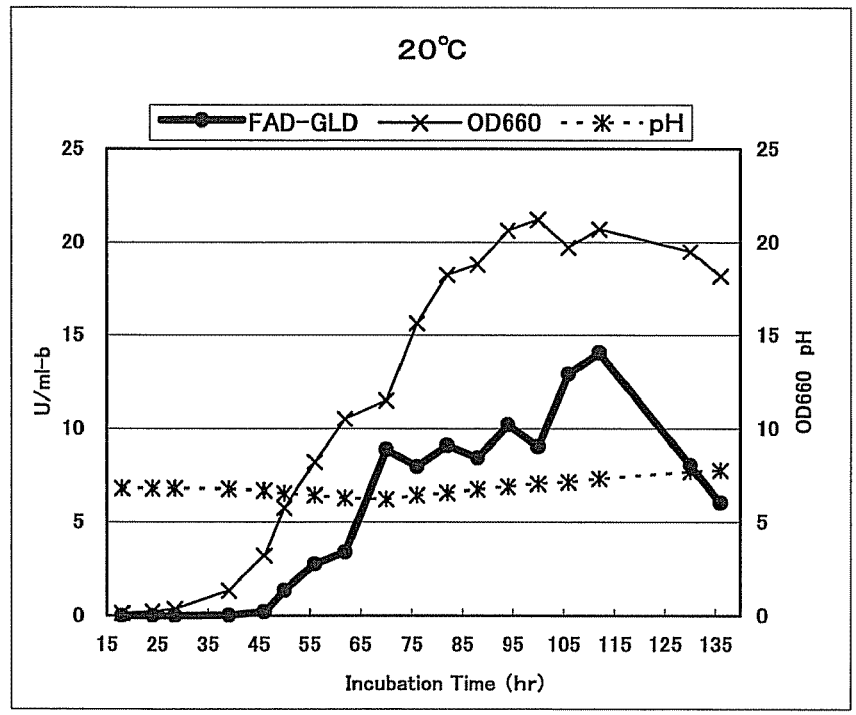
FIG. 9 is a graph showing the relation of the culture phase of GDH (the predicted signal peptide was removed) derived from wild type *A. terreus* at 20° C. at Kd•P of 0.5 with the turbidity (OD), pH and the GDH activity of microbial cells.
Figure 10:
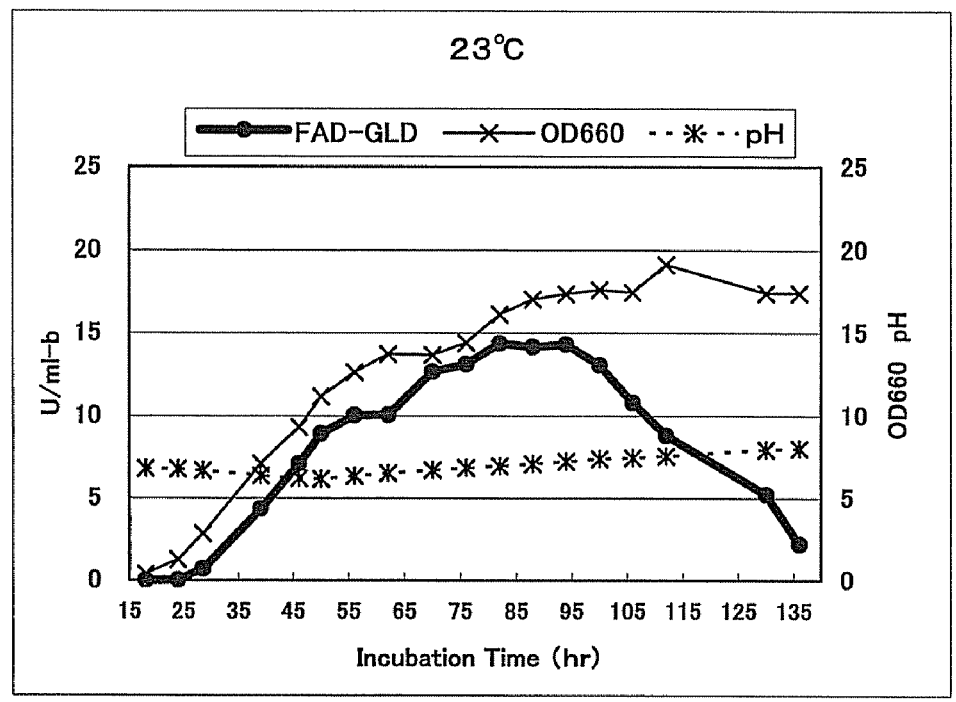
FIG. 10 is a graph showing the relation of the culture phase of GDH (the predicted signal peptide was removed) derived from wild type *A. terreus* at 23° C. at Kd•P of 0.5 with the turbidity (OD), pH and the GDH activity of microbial cells.
Figure 11:
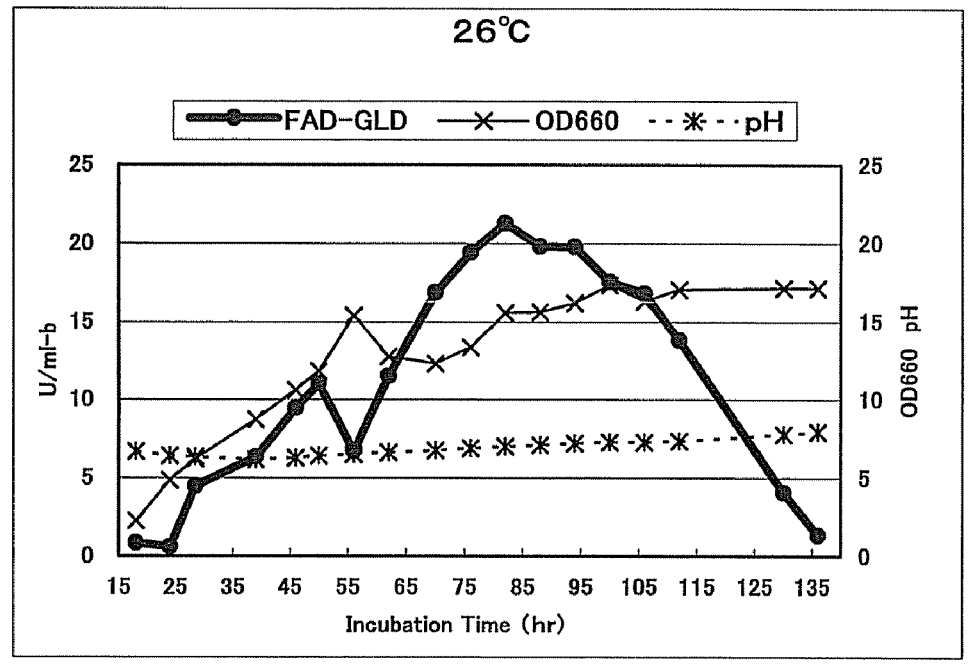
FIG. 11 is a graph showing the relation of the culture phase of GDH (the predicted signal peptide was removed) derived from wild type *A. terreus* at 26° C. at Kd•P of 0.5 with the turbidity (OD), pH and the GDH activity of microbial cells.
Figure 12:
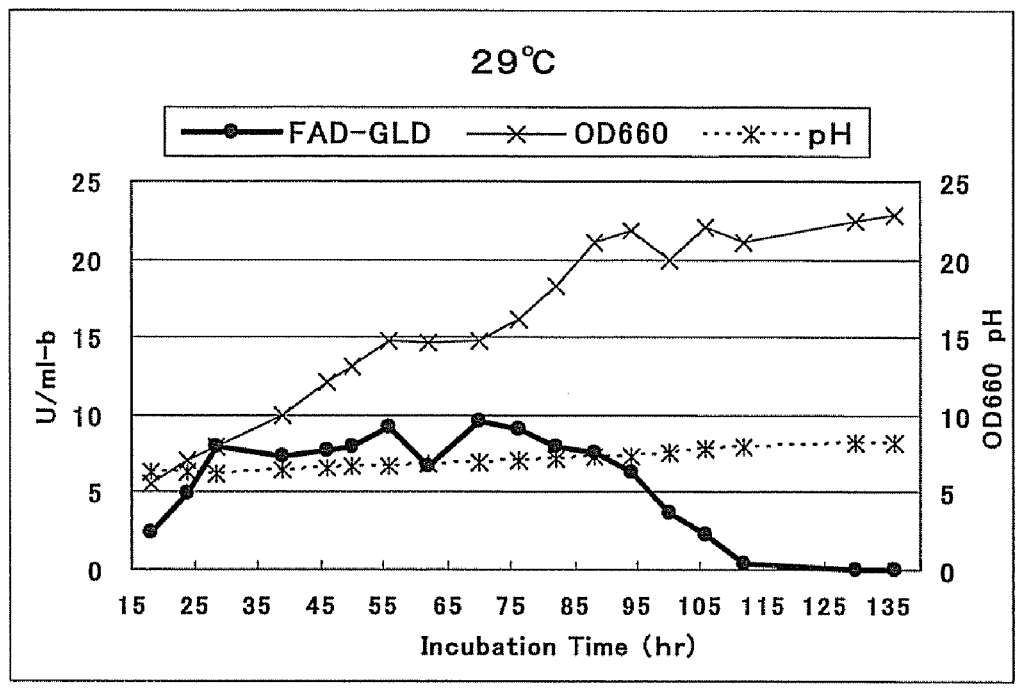
FIG. 12 is a graph showing the relation of the culture phase of GDH (the predicted signal peptide was removed) derived from wild type *A. terreus* at 29° C. at Kd•P of 0.5 with the turbidity (OD), pH and the GDH activity of microbial cells.

These transformants were cultured in the liquid medium of TB medium using the 10 L jar fermenter for 1 to 2 days. The microbial cells at each culture phase were collected, and disrupted with ultrasonic wave to identify the GDH activity. The relations of the culture phase of the transformant with OD, pH and the GDH activity are shown in Tables 1, 2 and 3 and FIGS. 2, 3 and 4. *Aspergillus oryzae* wild type strain was cultured in the liquid medium (1% malt extract, 1.5% soy bean peptide, 0.1% MaSO$_4$.7H$_2$O, 2% glucose, 0.5 mM p-benzoquinone, 0.1 mM EDTA, pH 6.5) using the 10 L jar fermenter at 30° C. for one day, and the GDH activity in or out of the microbial cells was measured. As a result, the GDH activity was about 0.2 U/mL of the medium (mL, broth) in all cases.

In the present patent, the expressed amounts are compared by comparing the GDH activity value per 1 mL of the medium.

In the wild type FAD-GDH (WT), the peak (6.6 U/mL-b (enzyme unit (U) per 1 mL of medium)) was observed at 16 to 18 hours of the culture, and then the activity was decreased. Meanwhile, in the modified FAD-GDH S2, the peak (72 to 73 U/mL-b) was observed at 22 to 25 hours of the culture, in S3 the peak (74 to 75 U/mL-b) was observed at 20 to 23 hours of the culture, and the GDH activity thereafter was decreased as was the case with WT.

Comparing culture titers in the respective peaks, it was revealed that the productivity of GDH was increased by 10 times or more by deleting the amino acid sequence thought to be the signal peptide.

Comparing the specific activity (U/mg) of FAD-GDH purified preparations before and after deleting the signal peptide, the specific activity was 270 U/mg in the wild type FAD-GDH (WT) whereas was 670 U/mg in the modified FAD-GDH S2 after the deletion. Thus, the specific activity was increased by 2.5 times. It is suggested that the specific activity is also increased by deleting the signal peptide.

Even considering the increase of the specific activity, the activity seems to be increased by at least 4.4 times.

Furthermore, as a result of an extensive study, we discovered that FAD-GDH derived from the filamentous fungus reduced its stability in a pH area of pH 7.1 or higher. In this study, it was revealed that it was important to control pH to 7.1 to 7.3 or lower and preferably 7.1 or lower in the culture of recombinant FAD-GDH derived from the filamentous fungus. It was confirmed that the peak of the GDH activity could be kept by controlling to be the pH or lower in the culture.

In the method for producing recombinant glucose dehydrogenase derived from the filamentous fungi, when the mutation was introduced into the signal sequence present in the N terminal region, the controlled pH can be raised to 7.3.

Example 2

Introduction of Glucose Dehydrogenase Gene Derived from *Aspergillus terreus* (Hereinafter Abbreviated as ATGDH) into *Escherichia coli*

For the ATGDH gene, mRNA was prepared from microbial cells of *Aspergillus terreus* (deposit number NBRC33026 registered at Biological Resource Center, National Institute of Technology and Evaluation), and cDNA was synthesized. Two oligo DNA shown in SEQ ID NOS:13 and 14 were synthesized, and the ATGDH gene (gene sequence in which the predicted signal peptide sequence had been deleted) was amplified using the prepared cDNA as the template and using KOD-Plus (supplied from Toyobo Co., Ltd.). The resulting DNA fragment was treated with the restriction enzymes NdeI and BamHI, and inserted into NdeI-BamHI sites in pBluescript (the NdeI site had been introduced to match a NdeI recognition sequence ATG to a translation initiation codon ATG of LacZ) to construct the recombinant plasmid. This plasmid was introduced into Competent High DH5α (supplied from Toyobo Co., Ltd.). The plasmid was extracted according to the standard method, and the base sequence of the ATGDH gene was determined (SEQ ID NO:11). The amino acid residues deduced from the DNA sequence were 568 amino acids (SEQ ID NO:12).

These transformants were cultured in 50 mL of the LB medium containing 100 μg/mL of ampicillin at 30° C. overnight, and again cultured in 50 mL of the LB medium containing 100 μg/mL of ampicillin at 30° C. for 8 hours to prepare an inoculum.

The prepared inoculum was cultured in the liquid of the TB medium containing 100 μg/mL of ampicillin in the range of Kd•P 0.5 to 1.5 using the 10 L jar fermenter for 6 days. The microbial cells at each culture phase were collected, and disrupted with ultrasonic wave to identify the GDH activity. The relations of the culture phase of the transformant with OD, pH and the GDH activity are shown in Tables 4, 5, 6 and 7 and FIGS. 5, 6, 7 and 8. *Aspergillus terreus* wild type strain was cultured in the liquid medium (1% malt extract, 1.5% soy bean peptide, 0.1% MaSO$_4$.7H$_2$O, 2% glucose, 0.5 mM p-benzoquinone, 0.1 mM EDTA, pH 6.5) using the 10 L jar fermenter at 30° C. for one day, and the GDH activity in the microbial cells was measured. As a result, about 0.1 U/mL of medium was the peak.

Meanwhile, in the recombinant FAD-GDH, the activity of about 9 to 21 U/mL-b was observed in the peaks, and the culture titers were increased by about 100 to 200 times. Examining the culture condition, when Kd•P was set to a low value 0.5, the culture titer was increased by about 1.5 times than in the case of Kd•P 0.75 and about 2 times than in the case of Kd•P 1 to 1.5. It was confirmed that when Kd•P was set to 2 or more, the culture titer was about 5 U/mL-b.

For the culture temperature, the relations of the culture phase with OD, pH and the GDH activity are shown in Tables 8, 9, 10 and 11 and FIGS. 9, 10, 11 and 12. The culture temperature at 26 to 28° C. is optimal, and it is necessary to culture at least at 23 to 28° C. If cultured at 29° C. or higher, the culture titer tended to reduce by half.

Also in the culture of the transformant with recombinant ATGDH gene, it is extremely important to keep the pH of the medium 7.3 or lower in order to keep the enzyme activity stably. In ATGDH, it seemed to be necessary to terminate the culture at lower pH than in AOGDH.

In the ATGDH gene, the DNA sequence of the predicted signal peptide (MLGKLSFLSALSLAVAATLSNSTSA) (SEQ ID NO:17) sequence was deleted from the DNA sequence encoding FAD-GDH derived from *Aspergillus terreus*. In the transformant containing the signal peptide, the amount of expressed FAD-GDH was poor as was the case with FAD-GDH derived from *A. oryzae*. Thus, the culture was initially studied using the transformant containing no signal peptide.

TABLE 1

| Sampling time hr | Wild type | | |
|---|---|---|---|
| | OD | pH | Act (U/ml) |
| 16 | 11.9 | 6.8 | 6.5 |
| 18 | 14.2 | 7.1 | 6.6 |
| 20 | 15.2 | 7.3 | 4.9 |
| 22 | 15.7 | 7.5 | 1.7 |
| 23 | 16.2 | 7.6 | 1.1 |
| 24 | 16.8 | 7.7 | 0.9 |
| 25 | 16.8 | 7.7 | 0.6 |
| 26 | 16.7 | 7.8 | 0.4 |
| 28 | 17.8 | 8.0 | 0.3 |
| 30 | 18.1 | 8.1 | 0.2 |

TABLE 2

| Sampling time hr | S2 OD | pH | Act Act(U/ml) |
|---|---|---|---|
| 16 | 5.8 | 6.7 | 14.1 |
| 18 | 9.3 | 6.6 | 47.0 |
| 20 | 11.4 | 6.7 | 63.5 |
| 22 | 14.0 | 7.0 | 72.2 |
| 23 | 14.5 | 7.1 | 72.8 |
| 24 | 15.1 | 7.2 | 73.3 |
| 25 | 15.8 | 7.3 | 71.6 |
| 26 | 16.5 | 7.5 | 49.9 |
| 28 | 17.3 | 7.7 | 36.2 |
| 30 | 17.5 | 7.9 | 24.4 |

TABLE 3

| Sampling time hr | S3 OD | pH | Act Act(U/ml) |
|---|---|---|---|
| 16 | 9.8 | 6.5 | 53.4 |
| 18 | 11.8 | 6.8 | 70.0 |
| 20 | 14.4 | 7.0 | 74.6 |
| 22 | 15.3 | 7.2 | 74.6 |
| 23 | 15.6 | 7.3 | 74.0 |
| 24 | 15.9 | 7.5 | 63.5 |
| 25 | 16.0 | 7.6 | 46.7 |
| 26 | 16.2 | 7.7 | 29.8 |
| 28 | 17.6 | 7.9 | 24.5 |
| 30 | 16.9 | 8.3 | 1.4 |

TABLE 4

| Time | FAD-GLD U/ml | OD660 | U/OD | pH |
|---|---|---|---|---|
| 16 | 0.8 | 3.0 | 0.28 | 6.76 |
| 20 | 1.9 | 4.7 | 0.41 | 6.5 |
| 24 | 3.0 | 7.1 | 0.42 | 6.51 |
| 28 | 6.7 | 9.8 | 0.68 | 6.45 |
| 32 | 9.2 | 12.4 | 0.74 | 6.39 |
| 36 | 11.5 | 13.2 | 0.87 | 6.3 |
| 40 | 15.5 | 14.0 | 1.11 | 6.4 |
| 44 | 13.8 | 16.0 | 0.86 | 6.48 |
| 48 | 14.7 | 17.5 | 0.84 | 6.56 |
| 52 | 15.7 | 17.1 | 0.92 | 6.63 |
| 56 | 17.4 | 17.8 | 0.98 | 6.73 |
| 60 | 17.4 | 19.4 | 0.90 | 6.8 |
| 64 | 16.3 | 20.7 | 0.79 | 6.84 |
| 68 | 13.6 | 19.6 | 0.69 | 6.93 |
| 72 | 14.6 | 21.5 | 0.68 | 6.94 |
| 76 | 15.2 | 21.9 | 0.70 | 7.02 |
| 80 | 13.9 | 23.2 | 0.60 | 7.09 |
| 84 | 13.4 | 24.6 | 0.55 | 7.19 |
| 88 | 10.2 | 20.2 | 0.51 | 7.23 |

TABLE 5

| Time | FAD-GLD U/ml | OD660 | U/OD | pH |
|---|---|---|---|---|
| 16 | 0.4 | 2.2 | 0.19 | 6.8 |
| 20 | 2.0 | 6.1 | 0.34 | 6.51 |
| 24 | 3.2 | 9.1 | 0.35 | 6.47 |
| 28 | 4.7 | 13.7 | 0.35 | 6.37 |
| 32 | 7.3 | 15.7 | 0.46 | 6.34 |
| 36 | 12.4 | 17.1 | 0.72 | 6.46 |
| 40 | 11.3 | 18.1 | 0.63 | 6.63 |
| 44 | 11.6 | 20.8 | 0.56 | 6.76 |
| 48 | 11.7 | 20.7 | 0.56 | 6.87 |
| 52 | 10.2 | 20.1 | 0.51 | 6.96 |
| 56 | 9.8 | 21.0 | 0.47 | 7.11 |

TABLE 5-continued

| Time | FAD-GLD U/ml | OD660 | U/OD | pH |
|---|---|---|---|---|
| 60 | 8.9 | 21.9 | 0.41 | 7.23 |
| 64 | 7.8 | 23.6 | 0.33 | 7.34 |
| 68 | 6.6 | 24.5 | 0.27 | 7.47 |
| 72 | 5.5 | 24.5 | 0.22 | 7.51 |
| 76 | 4.3 | 26.0 | 0.16 | 7.63 |
| 80 | 3.1 | 27.1 | 0.11 | 7.71 |
| 84 | 2.2 | 27.1 | 0.08 | 7.86 |
| 88 | 1.2 | 23.9 | 0.05 | 7.97 |

TABLE 6

| Time | FAD-GLD U/ml | OD660 | U/OD | pH |
|---|---|---|---|---|
| 16 | 0.2 | 2.1 | 0.09 | 6.83 |
| 20 | 2.3 | 7.0 | 0.33 | 6.51 |
| 24 | 3.7 | 11.0 | 0.33 | 6.49 |
| 28 | 9.9 | 15.8 | 0.63 | 6.27 |
| 32 | 10.0 | 18.4 | 0.54 | 6.44 |
| 36 | 9.8 | 20.9 | 0.47 | 6.74 |
| 40 | 8.1 | 21.2 | 0.38 | 6.92 |
| 44 | 6.5 | 21.6 | 0.30 | 7.1 |
| 48 | 5.8 | 21.9 | 0.26 | 7.32 |
| 52 | 4.4 | 20.5 | 0.22 | 7.46 |
| 56 | 2.9 | 20.4 | 0.14 | 7.62 |
| 60 | 1.6 | 22.3 | 0.07 | 7.75 |
| 64 | 0.7 | 23.6 | 0.03 | 7.86 |
| 68 | 0.4 | 24.6 | 0.02 | 8.18 |

TABLE 7

| Time | FAD-GLD U/ml | OD660 | U/OD | pH |
|---|---|---|---|---|
| 16 | 0.2 | 2.1 | 0.10 | 6.83 |
| 20 | 3.2 | 8.4 | 0.38 | 6.54 |
| 24 | 4.5 | 14.5 | 0.31 | 6.44 |
| 28 | 9.4 | 17.7 | 0.53 | 6.66 |
| 32 | 8.3 | 19.3 | 0.43 | 6.94 |
| 36 | 4.5 | 20.5 | 0.22 | 7.3 |
| 40 | 3.0 | 19.3 | 0.16 | 7.6 |
| 44 | 1.8 | 19.2 | 0.09 | 7.74 |
| 48 | 1.0 | 19.4 | 0.05 | 7.8 |
| 52 | 0.4 | 18.6 | 0.02 | 8.01 |
| 56 | 0.1 | 19.1 | 0.01 | 8.09 |
| 60 | 0.0 | 20.2 | 0.00 | 8.11 |
| 64 | 0.0 | 19.6 | 0.00 | 8.22 |
| 68 | 0.0 | 18.9 | 0.00 | 8.42 |

TABLE 8

| Time | FAD-GLD U/ml | OD660 | U/OD | pH |
|---|---|---|---|---|
| 18 | 0.0 | 0.1 | 0.01 | 6.81 |
| 24 | 0.0 | 0.2 | 0.02 | 6.81 |
| 28.5 | 0.0 | 0.4 | 0.02 | 6.8 |
| 39 | 0.0 | 1.4 | 0.01 | 6.78 |
| 46 | 0.2 | 3.2 | 0.07 | 6.68 |
| 50 | 1.4 | 5.8 | 0.24 | 6.53 |
| 56 | 2.7 | 8.2 | 0.33 | 6.45 |
| 62 | 3.4 | 10.5 | 0.32 | 6.28 |
| 70 | 8.9 | 11.5 | 0.77 | 6.24 |
| 76 | 8.0 | 15.7 | 0.51 | 6.44 |
| 82 | 9.1 | 18.2 | 0.50 | 6.57 |
| 88 | 8.4 | 18.8 | 0.45 | 6.75 |
| 94 | 10.2 | 20.6 | 0.49 | 6.89 |
| 100 | 9.0 | 21.2 | 0.43 | 7.05 |
| 106 | 12.9 | 19.7 | 0.66 | 7.14 |
| 112 | 14.0 | 20.7 | 0.68 | 7.31 |
| 130 | 8.0 | 19.5 | 0.41 | 7.69 |
| 136 | 6.0 | 18.2 | 0.33 | 7.76 |

TABLE 9

| Time | FAD-GLD U/ml | OD660 | U/OD | pH |
|---|---|---|---|---|
| 18 | 0.0 | 0.4 | 0.01 | 6.81 |
| 24 | 0.0 | 1.3 | 0.01 | 6.79 |
| 28.5 | 0.7 | 2.9 | 0.24 | 6.7 |
| 39 | 4.4 | 7.1 | 0.61 | 6.37 |
| 46 | 7.1 | 9.3 | 0.76 | 6.22 |
| 50 | 8.9 | 11.2 | 0.80 | 6.19 |
| 56 | 10.0 | 12.7 | 0.79 | 6.36 |
| 62 | 10.0 | 13.7 | 0.73 | 6.53 |
| 70 | 12.7 | 13.7 | 0.93 | 6.72 |
| 76 | 13.1 | 14.4 | 0.91 | 6.85 |
| 82 | 14.4 | 16.1 | 0.89 | 6.97 |
| 88 | 14.2 | 17.1 | 0.83 | 7.1 |
| 94 | 14.3 | 17.4 | 0.82 | 7.25 |
| 100 | 13.1 | 17.6 | 0.74 | 7.4 |
| 106 | 10.8 | 17.5 | 0.62 | 7.45 |
| 112 | 8.8 | 19.1 | 0.46 | 7.57 |
| 130 | 5.2 | 17.4 | 0.30 | 7.96 |
| 136 | 2.2 | 17.4 | 0.13 | 8.03 |

TABLE 10

| Time | FAD-GLD U/ml | OD660 | U/OD | pH |
|---|---|---|---|---|
| 18 | 0.8 | 2.3 | 0.37 | 6.69 |
| 24 | 0.6 | 4.9 | 0.12 | 6.43 |
| 28.5 | 4.5 | 6.2 | 0.72 | 6.35 |
| 39 | 6.3 | 8.7 | 0.72 | 6.18 |
| 46 | 9.5 | 10.6 | 0.89 | 6.28 |
| 50 | 11.0 | 11.8 | 0.93 | 6.41 |
| 56 | 6.7 | 15.4 | 0.44 | 6.52 |
| 62 | 11.5 | 12.8 | 0.90 | 6.63 |
| 70 | 16.9 | 12.3 | 1.37 | 6.77 |
| 76 | 19.4 | 13.3 | 1.46 | 6.89 |
| 82 | 21.3 | 15.6 | 1.37 | 7.02 |
| 88 | 19.8 | 15.6 | 1.27 | 7.1 |
| 94 | 19.8 | 16.2 | 1.22 | 7.22 |
| 100 | 17.6 | 17.4 | 1.01 | 7.28 |
| 106 | 16.8 | 16.3 | 1.03 | 7.28 |
| 112 | 13.8 | 17.1 | 0.81 | 7.34 |
| 130 | 4.1 | 17.2 | 0.24 | 7.77 |
| 136 | 1.3 | 17.2 | 0.08 | 7.94 |

TABLE 11

| Time | FAD-GLD U/ml | OD660 | U/OD | pH |
|---|---|---|---|---|
| 18 | 2.4 | 5.6 | 0.43 | 6.31 |
| 24 | 5.0 | 7.0 | 0.71 | 6.28 |
| 28.5 | 7.9 | 7.9 | 1.01 | 6.21 |
| 39 | 7.4 | 10.0 | 0.74 | 6.42 |
| 46 | 7.8 | 12.1 | 0.64 | 6.55 |
| 50 | 8.0 | 13.1 | 0.61 | 6.66 |
| 56 | 9.2 | 14.8 | 0.62 | 6.75 |
| 62 | 6.7 | 14.7 | 0.45 | 6.85 |
| 70 | 9.6 | 14.8 | 0.65 | 6.98 |
| 76 | 9.0 | 16.1 | 0.56 | 7.12 |
| 82 | 8.0 | 18.3 | 0.44 | 7.17 |
| 88 | 7.6 | 21.1 | 0.36 | 7.27 |
| 94 | 6.3 | 21.8 | 0.29 | 7.38 |
| 100 | 3.7 | 20.0 | 0.18 | 7.58 |
| 106 | 2.3 | 22.1 | 0.10 | 7.78 |
| 112 | 0.4 | 21.1 | 0.02 | 7.93 |
| 130 | 0.1 | 22.5 | 0.00 | 8.18 |
| 136 | 0.0 | 22.8 | 0.00 | 8.2 |

Tables 1 to 3 show the relations of the culture phase of each mutant in the 10 L jar fermenter culture with the values of microbial cell turbidity (OD), pH and the GDH activity in the medium. Tables 1, 2 and 3 correspond to FIGS. 2, 3 and 4, respectively.

Tables 4 to 7 show the relations of the culture phase at Kd•P 0.5, 0.75, 1 or 1.5 in the 10 L jar fermenter culture with the values of microbial cell turbidity (OD), pH and the GDH activity in the medium. Tables 4, 5, 6 and 7 correspond to FIGS. 5, 6, 7 and 8, respectively.

Tables 8 to 11 show the relations of the culture phase at temperature of 20, 23, 26 or 30° C. in the 10 L jar fermenter culture with the values of microbial cell turbidity (OD), pH and the GDH activity in the medium. Tables 8, 9, 10 and 11 correspond to FIGS. 9, 10, 11 and 12, respectively.

INDUSTRIAL APPLICABILITY

The present invention enables to produce glucose dehydrogenase derived from *Aspergillus oryzae* on a large scale by the use of recombinant *Escherichia coli*. By the present invention, it becomes possible to produce glucose dehydrogenase which does not act upon maltose in a broad sense and is suitable for the glucose sensor and the like.

The invention claimed is:

1. An isolated DNA sequence encoding the amino acid sequence of SEQ ID NO: 4, except that a part or all of a DNA sequence encoding a signal peptide sequence present at the N terminus of the amino acid sequence is substituted and/or deleted.

2. A recombinant vector comprising the isolated DNA sequence of claim 1.

3. A transformant comprising the recombinant vector according to claim 2.

4. The DNA sequence of claim 1, which encodes the amino acid sequence of SEQ ID NO: 4, except that a part or all of the amino acid sequence of SEQ ID NO: 18 is substituted or deleted.

5. The DNA sequence of claim 1, which encodes the amino acid sequence of SEQ ID NO: 4, except that the amino acid sequence of SEQ ID NO: 18 is deleted.

6. The DNA sequence of claim 1, which encodes the amino acid sequence of SEQ ID NO: 10.

* * * * *